US008574413B2

(12) United States Patent
Mosley et al.

(10) Patent No.: US 8,574,413 B2
(45) Date of Patent: Nov. 5, 2013

(54) ELECTRODES, SENSORS AND METHODS FOR MEASURING COMPONENTS IN WATER

(75) Inventors: Michael D. Mosley, Hazelwood, MO (US); Paul Decker, Creve Coeur, MO (US)

(73) Assignee: Digital Concepts of Missouri, Inc., Maryland Heights, MO (US)

( * ) Notice: Subject to any disclaimer, the term of this patent is extended or adjusted under 35 U.S.C. 154(b) by 98 days.

(21) Appl. No.: 13/051,106

(22) Filed: Mar. 18, 2011

(65) Prior Publication Data
US 2012/0234696 A1   Sep. 20, 2012

(51) Int. Cl.
*G01N 27/30*   (2006.01)
*G01N 27/333*   (2006.01)

(52) U.S. Cl.
USPC ........ 204/416; 204/433; 205/775; 435/287.1; 422/82.01; 422/68.1; 324/438

(58) Field of Classification Search
USPC ................ 204/416, 433; 205/775; 422/82.01, 422/68.1; 435/287.1; 324/438
See application file for complete search history.

(56) References Cited

U.S. PATENT DOCUMENTS

| | | | |
|---|---|---|---|
| 2,350,378 A | 6/1944 | Wallace | |
| 2,382,734 A | 8/1945 | Marks | |
| 3,258,682 A | 6/1966 | Maurer | |
| 3,298,944 A | 1/1967 | Luck | |
| 3,361,150 A | 1/1968 | Horner | |
| 3,402,116 A | 9/1968 | Kaltenhauser et al. | |
| 3,413,199 A | 11/1968 | Morrow, Jr, | |
| 3,591,481 A | 7/1971 | Riseman | |
| 3,591,482 A | 7/1971 | Neff et al, | |
| 3,742,594 A | 7/1973 | Kleinberg | |
| 3,790,463 A | 2/1974 | Gealt | |
| 3,902,982 A | 9/1975 | Nakagawa | |
| 3,959,087 A | 5/1976 | Morrow | |
| 4,119,498 A | 10/1978 | Edwall et al. | |
| 4,129,479 A | 12/1978 | Morrow | |
| 4,199,412 A | 4/1980 | Battaglia et al. | |
| 4,224,154 A | 9/1980 | Steininger | |
| 4,681,116 A | 7/1987 | Settler | |
| 4,818,365 A | 4/1989 | Kinlen et al. | |
| 4,940,946 A | 7/1990 | Nazaryan | |
| 5,213,675 A | 5/1993 | Yamaguchi et al. | |
| 6,238,553 B1 * | 5/2001 | Lin ................................ | 210/94 |
| 6,627,450 B1 * | 9/2003 | Taylor et al. .................. | 436/125 |
| 6,653,842 B2 | 11/2003 | Mosley et al. | |
| 2003/0112012 A1 * | 6/2003 | Mosley et al. ................ | 324/446 |
| 2005/0258039 A1 | 11/2005 | Warburton et al. | |

OTHER PUBLICATIONS

Pham et al. (Analytica Chimica Acta 671 (2010) 36-40).*
Schwake et al. (Sensors and Actuators B 46, 1998, 242-248).*
Henry C. Marks and G.L. Bannister, Amperometric Methods in the Control of Water Chlorination—Analytical Chemistry, pp. 200-204.

* cited by examiner

*Primary Examiner* — J. Christopher Ball
*Assistant Examiner* — Jennifer Dieterle
(74) *Attorney, Agent, or Firm* — Senniger Powers LLP

(57) ABSTRACT

Improvements in references electrodes, halogen sensors, pH sensors, TDS sensors, combinations thereof, and related methods.

34 Claims, 10 Drawing Sheets

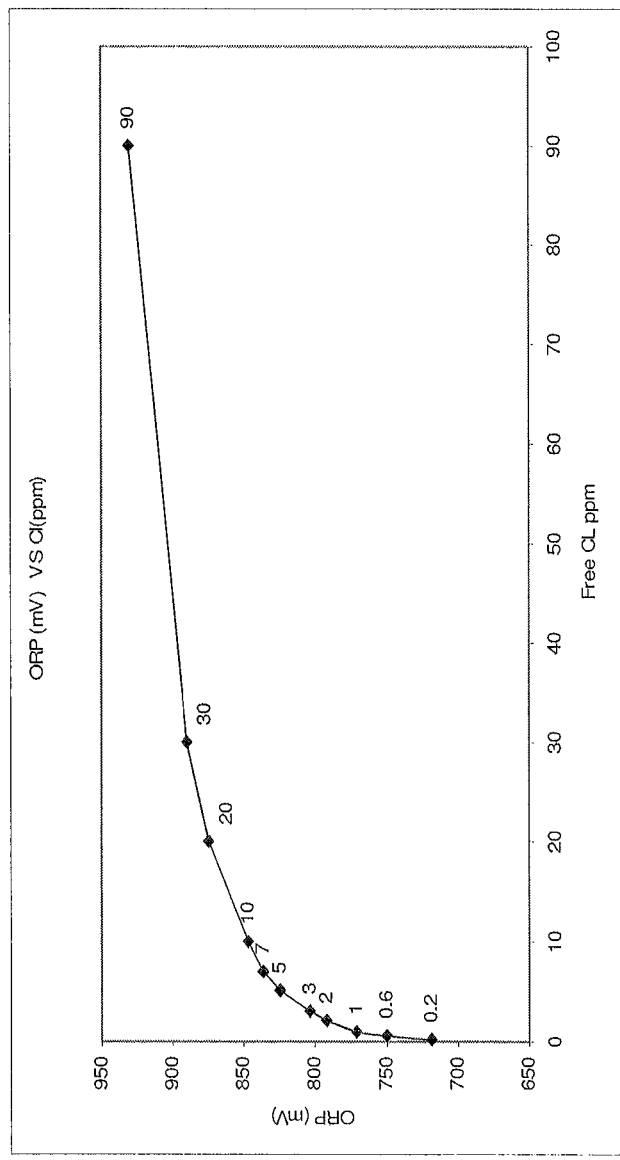
FIGURE PA1

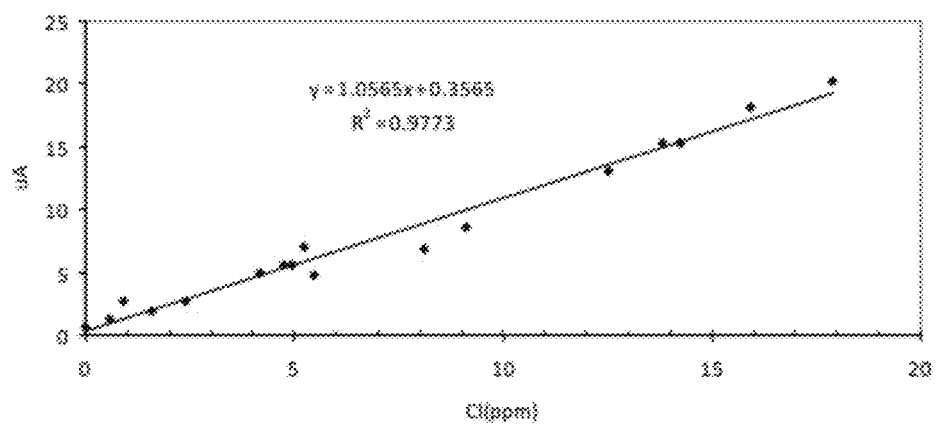
Fig. PA-2

ELECTRODES, SENSORS AND METHODS FOR MEASURING COMPONENTS IN WATER

BACKGROUND OF THE INVENTION

1. Field of the Invention

The present invention relates to electrochemical probes, and more particularly to electrochemical sensors for measuring certain characteristics of aqueous liquids, and components of such sensors.

2. Description of the Related Art

In many situations, it is desired to measure and to monitor a variety of characteristics of liquids, especially aqueous liquids, and often it is desirable to monitor such characteristics at frequent intervals—or even continuously. Such characteristics include the pH of the liquid, the total dissolved solids in the liquid, the temperature of the liquid, the concentration of ionic solutes such as chlorine species in the liquid, and the oxidation reduction potential (ORP) of the liquid (that is, the relative tendency of materials in the liquid to undergo oxidation or reduction—particularly the ability of the liquid to destroy bacteria in it). Many of these characteristics can be measured electrolytically.

Measurement of a liquid's characteristics such as pH, halide concentration, ORP and solute concentrations are of interest in a wide variety of industrial, commercial and domestic processes and situations. For example, many chemical processes are pH-, ORP- or solute-dependent. The pH, ORP or solute levels of effluents from factories are commonly of environmental concern.

The pH, halide concentration, ORP or solute level of water in particular is critical in many settings. For example, a setting familiar to many laypersons is in various water storage systems, such as air conditioning systems, swimming pools and spas. Therefore, for ease of explanation, much of the following discussion will be with reference to the swimming pool setting, although it should be borne in mind that the discussion is likewise applicable to any other situation in which the pH, halide concentration, ORP and/or solute level of a liquid is of interest.

In a swimming pool, the quality of the water is closely related to the pH and ORP of the water. In swimming pools, the ORP of the water is a measure of the free chlorine level in the water, and the solute level may be of chlorine species resulting from addition of, for example, hypochlorous acid or sodium hypochlorite, the concentrations of free chlorine and other chlorine species being related to the biological antiseptic quality of the water.

Therefore, the pH and concentration of chlorine species ("chlorine level") of swimming pool water must be monitored to ensure that an adequate water quality level is maintained. Conventionally, this is carried out by hand and the owner or other caretaker in charge of maintaining the pool must repeatedly go to the pool with vials and chemicals, scoop out the water into the vials, shake the vials, compare the colors of the resulting solutions to those on charts coordinated with the pool volume to determine the amounts of chemicals to add to restore the proper pH and/or chlorine level, obtain those chemicals, measure them out and add them to the pool. Not only is this a cumbersome process, but if it is not carried out at frequent enough intervals, the quality of the pool water can become unacceptable very quickly. Thus, for example, if the pool caretaker is away for a several days, he or she may return to find a pool filled with murky water. Or the pH or chlorine level may fall out of acceptable range too soon before the next testing and the water may become unhealthful, and the pool caretaker may not realize that fact until it is too late. Therefore, it is desirable to have a pH monitor and/or an ORP monitor that would carry out the measurement task automatically and frequently even continuously—on a real time basis.

Sensors for such measurements often operate on a potentiometric electrochemical principle that incorporates a reference electrode and a sensing electrode. Conventional reference electrodes for use in such potentiometric electrochemical measurements typically incorporate an internal reference fill solution in contact with an electrode in contact with a test solution through a porous junction, which allows a slow leak of the internal reference fill solution to provide the necessary electrolytic contact with the liquid being tested. A metal or electrochemical electrode in contact with the test solution completes the circuit and an electrical potential on the reference electrode remains relatively constant while the sensing electrode responds to chemical changes in the test solution.

Conventional electrodes of this type suffer from several drawbacks when applied to certain measurement environments, such as long-term unattended monitoring of pool or spa water. For example, because leakage of the internal reference fill solution through the porous junction into the tested environment is necessary to provide electrolytic conductivity between the internal reference fill solution and the tested environment, the useful life of the reference electrode is limited. Moreover, a high rate of leakage is desirable to produce a low electrical impedance of the reference electrode. Moreover, in a pipe mounted system, the flow of test solution flowing over the electrode exacerbates the high leakage rate. Thus, while low electrical impedance is desirable for accurate measurements because it reduces noise, the high leakage rate employed in such conventional reference electrodes to produce the desired low electrical impedance severely limits the life of the electrode and the electrode must be frequently refilled with fresh internal solution or replaced.

Such conventional reference electrodes suffer from other disadvantages as well. For example, they tend to be fragile, typically being encased in glass. Moreover, they often are limited in operational orientation. In other words, because the reference fill solution of the electrode is a liquid, it readily flows as a result of gravity. Thus, the relative orientation of the electrode with respect to the reference fill solution and the reference fill solution with respect to the porous junction depends on the spatial orientation of the electrode and so the electrode assembly in the test solution must be oriented vertically so that the reference fill solution is properly oriented in the electrode. Indeed, silver/silver chloride reference electrodes suspended in glass-encased fill solutions have been employed in combination with antimony electrodes in some pH sensors, with all the attendant disadvantages of glass membranes and fill solutions noted above.

Reference electrodes according to the manufacturer of the reference electrode described in U.S. Pat. No. 7,462,267 are also available. They use a gelled polyelectrolyte internal fill solution to reduce the osmotic ionic pressure resulting from the high ionic concentration in the internal fill solution relative to the low ionic content of surrounding solution. Missing from the discussion was the impact of the porosity of the frit used to separate the internal fill solution from the environment and the necessity of mechanical fixture of the porous frit. Such electrodes were procured and evaluated and found not only to display a marked sensitivity to changes in the amount of chloride based salts in solution but due to the high porosity (35 microns) that the fill solution would leach out during regular use over a short time from (2 months). Also with regard to the placement of the frit it was found that during shipment that differences in atmospheric pressure routinely push the frit from the electrode body resulting in complete loss of electrolyte.

Potentiometric solid state sensors, in which measurement is based on ion specific voltage developed between a reference electrode and a measuring sensor, have been described in scientific publications, but their commercialization is extremely limited, and no large-scale production process has been developed. In any event, they also suffer from other serious disadvantages. They require frequent calibration, they suffer from significant drift, they have very limited lives, have limited applicability because some common salts damage their sensor membranes, are expensive (although, at about US $20, are less expensive than the previously mentioned meters), are affected substantially by temperature, and while they can be stored dry, they require about 24 hours for stabilization.

U.S. Pat. No. 5,497,091 describes a pH sensor that employs an antimony electrode in combination with a ceramic reference electrode, but provides no clear description of the ceramic reference electrode. However, known antimony-based pH sensors typically employ a polished antimony surface for enhanced sensitivity and so suffer from deteriorating sensitivity as they lose polish. In addition, known antimony-based pH sensors typically also suffer from substantial drift as the quality of the polish diminishes over time, and, as with the other pH sensors dependent on ion exchange between the fluid being tested and the fill solutions, known antimony-based pH sensors frequent recalibration and limited lifetimes due to gradual dilution of the fill solution. Moreover, because they employ a liquid fill solution, they must be maintained in a vertical position. Thus, state of the art reference electrodes for pH monitors are unsuitable for many uses, especially those in which a durable, inexpensive and readily available (or easy to manufacture) probe for frequent, accurate, real time pH measurements with low drift.

Monitors for measuring ORP also are available commercially. Their measurements are based on a voltage developed between a silver/silver chloride reference wire in an internal fill solution and a platinum wire isolated from the fill solution. Such monitors also suffer from serious drawbacks, including high cost (about US $250), unavailability in large quantities, limited life based on the fill solution, lengthy response time, the requirement of a soaker cap to keep the tip wet when not in use, and the requirement of all electrodes that employ fill solutions that that they be maintained in an almost vertical position to keep the electrodes in the tested fluid. Thus, as with the state of the art pH monitors, state of the art reference electrodes for ORP probes are unsuitable for many uses, especially those in which a durable, inexpensive and readily available (or easy to manufacture) probe for frequent, accurate, real time ORP measurements with low signal drift.

The reference electrode is paired with a sensing electrode correlated with the characteristic to be measured. As noted above, such characteristics may include the concentration of sanitizer such as chlorine and the total dissolved solids in the liquid.

With respect to the sanitizer level, it should be noted that, as mentioned above, many aquatic environments, such as pools and spas, contain certain chemicals to sanitize the water and to maintain its quality against a variety of organisms and other organic matter in it. A common approach to water treatment is to use some sort of oxidizing chemical to remove bacteria and impurities from it. For example, frequently, the oxidizing chemical employed is one that imparts a halogen such as bromine or, more commonly, chlorine to the water. Thus, the discussion below will often be directed specifically to chlorine, but it should be understood that it may be applied to other halogens as well.

Typically, in a swimming environment, chlorine is added until all the contaminants are oxidized with some "residual" amount left over to oxidize more over the course of time. This is referred to as "free chlorine." This residual amount establishes a sufficient chlorine level in the water to continue to oxidize (sanitize) more bacteria as they are produced and it is desired that the concentration of the halogen in the aquatic environment be maintained within a relatively narrow range so that the concentration is high enough to sanitize the water, but not so high as to be either wasteful or undesirable for human interaction. A common standard in pools is to keep the free chlorine between about 1 and about 3 parts per million (ppm) (as used herein, ppm measurements, are on a weight basis). In spas, the free chlorine leval is somewhat higher; generally about 3 to about 5 ppm.

Therefore, it is important to have an accurate way to carry out frequent or regular measurements of the level of halogen such as free chlorine in liquid aqueous environments, especially levels that are on the order of from about 1 to about 3 ppm. Unfortunately, however, the chemicals employed to sanitize the water interact with efforts to measure the halogen content of the water and so it is difficult to measure the halogen concentration accurately.

Further complexity is added by the characteristics and nature of the chlorine that is employed. In more detail, and with specific reference to the use of chlorine in swimming pools and spas, chlorine used to treat swimming water exists in two basic forms, unstabilized and stabilized. Common types of unstabilized chlorine are household bleach and granular sodium hypochlorite. Unstabilized chlorine is chemically unstable in water exposed to sunlight, especially direct sunlight. Sunlight breaks down chlorine over time to a point where it no longer has a sanitizing effect on the water. Indeed, the effect of sunlight on unstabilized chlorine can be quite dramatic. For instance, the chlorine level of water treated with unstabilized chlorine can be reduced from several ppms to almost 0 by exposure to direct sunlight for a half an hour at moderate temperatures. Therefore, water containing unstabilized chlorine as a sanitizer requires regular addition of chlorine to maintain sufficient chlorine levels.

Stabilized chlorine, on the other hand, is chemically modified to last longer in sunlight. Thus, the chlorine used to treat outdoor pools is almost exclusively stabilized chlorine. Common types of stabilized chlorine are trichloro-n-triazine trione tablets and sodium dichloro, in granular and tablet form. Unstabilized chlorine can also be stabilized by adding granular cyanuric acid to the water along with it. Accordingly, cyanuric acid is a common ingredient in stabilized chlorine. Cyanuric acid binds chemically to some of the chlorine holding it in reserve to slow its rapid deterioration in sunlight.

By contrast, indoor pools generally are not exposed to direct sunlight and so most indoor pools do not require use of stabilized chlorine. There are benefits in not using stabilized chlorine and pure cyanuric acid in particular. For example, cyanuric acid, a form of which all forms of stabilized chlorine contain, is toxic and in the United States, mandated limits have been instituted on the amount of cyanuric acid a pool may contain; typically about 140 ppm. Secondly, the only widely available test for cyanuric acid is a turbidity test that is subject to substantial error.

The presence of cyanuric acid also creates substantial difficulty in the determination of active chlorine levels in water. This difficulty in water containing cyanuric acid arises from the limitations of the various methods used to measure chlorine and the notion of "free" or residual chlorine. Of the various test methods for determining chlorine concentration, the DPD (N,N-Diethyl-p-phenylenediamine) test is the most common. Its use has become common because of the expense and general unavailability of electronic instruments needed by other methods.

The DPD test involves taking a sample of water and adding a reagent to it to effect a color change in it, then adding another reagent drop-wise to remove the color. The amount of residual chlorine is related to the number of drops required to remove the color from the sample. This test, however, has several drawbacks. For example, there is a limit as to how much of the de-coloring reagent can be added after the initial color change reagent.

In fact, depending on the level of chlorine in the water, two tests may be required. If, after adding the color change reagent, the sample is extremely dark, dilution is required and so a smaller volume of sample is used for the second test. Also, the chemicals used have a finite shelf life, requiring the chemicals to be replenished. Chemical test strips based on this same color-change test mechanism based on the amount of chlorine to which they are exposed also may be used. The resulting color of the test strip is compared to a chart of colors that indicate a general range of chlorine associated with it. It is very difficult to pinpoint at levels around about 3 ppm by color matching, however, and so such tests are only a general indication of the amount of chlorine present. Moreover, the test strips also have a limited shelf life. Other tests employ an electronic sensor that generates a signal based on the chemical activity of free chlorine. The presence of cyanuric acid in the water interferes with the results such tests and so the results of measuring the level of free chlorine in water differ depending on whether or not the water contains cyanuric acid. Therefore, the presence or absence of cyanuric acid poses a serious challenge to the measurement and control of chlorine levels in a pool environment.

In some elaborate pool installations, the chlorination of the pool system is controlled automatically with an electronic chlorine sensor mounted inline with a chlorine-dispensing mechanism. When and how much chlorine is added is determined by set points in the controller based on the output of this sensor. The initial set point is typically based on a reading from a DPD test.

However, a difficulty arises if stabilized chlorine is added to the water after initial setup. The degree to which the stabilized chlorine is a problem in chlorine measurement depends at least in part on the amount of cyanuric acid it introduces into the water and the type of electronic sensor used to measure the chlorine. Electronic sensors measure the actual real-time amount of free chlorine active in the water, but since cyanuric acid binds with some of the chlorine, the bound chlorine is not free and active and contributes only minimally to the electrical signal. Therefore, it remains largely unmeasured and if any cyanuric-based chlorine is introduced into the water after this there will be a difference between the results of a DPD test and the measured ppm using an electronic sensor. The DPD test will indicate a higher measurement of free chlorine than will the electronic sensor. This is because the reagent added to the water sample used by the DPD test to effect the color change effectively releases the bound chlorine from the cyanuric acid, allowing it to be measured.

If the DPD test is used to set the system up without cyanuric acid, the two results will be the same. However, if cyanuric acid is added later the displayed amount of chlorine on the electronic system will drop with respect to the DPD measurement and, depending on the set point, possibly start erroneously adding chlorine to the pool. This effect cannot be compensated for in a systematic way because the effect is variable depending on the relative levels of cyanuric acid and chlorine and how much sunlight there is at the pool site, Nevertheless, it is still desirable to maintain at least a small amount of cyanuric acid for, without it, the chlorine breakdown cause(d) by the exposure to direct sunlight would produce an extraordinary and costly chlorine demand.

Several types of electronic sensors are used in automated measurement systems. The most common is an oxidation reduction potential (ORP) sensor, an example of which is discussed in U.S. Pat. No. 4,224,154 to Steininger. This type of sensor employs an electrode that is most affected by cyanuric acid.

The sensing mechanism of the sensor is based on the fact that adding an oxidizer such as chlorine to water generates a voltage between two electrodes of the sensor. One of the electrodes is an unpolarized reference electrode. The other electrode is a catalytically reactive noble metal such as platinum. The voltage generated between the electrodes is based on the simultaneous oxidation of impurities and the reduction of chlorine occurring in the process. The voltage output from this type of sensor is between 0 and about 900 millivolts. However, the response of the electrode is logarithmic; i.e., the greatest change in the output voltage occurs within the first 2-3 ppm of added chlorine with almost no correlation at higher levels.

Typically, an algorithm is used to relate the ORP signal to a ppm reading. However, the sensor's logarithmic response can produce wide variance in the reported ppm level. See, for example, FIG. 1. Exacerbating this effect is the fact that the presence of even small amounts of cyanuric acid can reduce the signal output by several tens of millivolts, Another difficulty encountered in using an ORP sensor to measure sanitizer level is that it is highly pH-dependent—on the order of 50 mill volts per pH change. Therefore, the output of ORP sensors in an automated system frequently requires adjustment, which is clearly undesirable from an operational standpoint.

Another type of chlorine sensor is a galvanic sensor, which is based on the galvanic coupling of dissimilar metals through electrode depolarization (See U.S. Pat. No. 3,413,199 to Morrow and U.S. Pat. No. 2,382,734 to Marks). Depending on the metals involved, a measurable current that is linearly proportional to the amount of free chlorine in ppm flows between the electrodes. See FIG. 2. The current flow is due to the anode being oxidized and chlorine being reduced at the cathode. These reactions proceed as long as there is a source of chlorine being reduced.

This technique requires a constant flowrate of water past the electrodes to replenish the chlorine being reduced at the cathode. Since the current flow is linear, the signal can be more easily calibrated to specific amounts of chlorine as opposed to the logarithmic curve from the ORP sensor. While the signal is also somewhat sensitive to pH, in a limited pH range between 6.5 and 8.0, the effect can be compensated for electronically or by software. Nevertheless, if the pH varies over a wide range or is unstable, a buffering agent may need to be added to the sample to stabilize the pH in the range of measurement.

The signal measured in a galvanic sensor also is sensitive to temperature, requiring further compensation, but the compensation usually is easily achieved in the normal range of temperatures encountered in pools and spas (generally about 65° F. to about 110° F.).

The type of electrode employed in such sensors is much less affected by the presence of cyanuric acid than are those of the DPD sensors; however, as noted previously, it will also indicate less chlorine with respect to the DPD measurement in systems with cyanuric acid. Nevertheless, it will not display the wide deviations found in ORP measurements. The impact on automated systems is minimized by the fact that the dosage set point can be reasonably set at a level of 1-3 ppm without causing wide fluctuations in dosage.

In any event, galvanic sensors also suffer from several drawbacks that also make their use problematic. For one thing, since the reaction is galvanic, the anode must be an electrically active metal and so it becomes oxidized over a period of time, which can lead to chemical changes on its surface that effect its sensitivity to chlorine. Also, depending on the level of electro-activity, the anode may begin to plate onto the cathode, further reducing the sensitivity. Therefore, some abrasive element such as corundum is commonly added into the flow cell to mitigate the accumulation of reactant byproducts on the electrode surfaces. Without this abrasion mechanism, the output from the sensor diminishes over a fairly short time—typically 1 to 2 weeks.

Galvanic sensors are also affected by the electrolytic conductivity of the water, usually requiring it to be below about 1000 micro-Siemens or about 500 ppm. This precludes their use in pools that use a salt chlorinator to generate chlorine electrolytically from sodium chloride added to the water. The conductivity in this water is on the order of about 6000 μS or about 3000 ppm. Although this type of sensor is superior to the ORP measurement, it still does not address the practical aspects of using it for long-term, unattended operation in pools and spas sufficiently.

Other types of sensors used in the detection of chlorine are amperometric in nature. Amperometric sensors use an applied bias voltage to establish a current flow based on the level of free chlorine. The detection mechanism is based on electrode depolarization, which is the same as that involved in galvanic sensors except that, since there is an applied voltage, the electrodes can be of the same material. The primary issues raised by amperometric sensors are corrosion resistance and catalytic activity. To address these issues, noble metals such as platinum or gold tend to be used for the electrodes. Noble metals do not display the oxidation effects to the degree seen with the galvanic sensor and are not particularly sensitive to electrolytic conductivity Although any electrochemical sensor will require some minimal amount of conductivity to function, this is not a problem in pools since the conductivity of most tap water is at least around 300 ppm.

The difficulties of amperometric measurement in pools and spas are primarily related to passivation of the anode and deposits of foreign matter on it. Various methods have been employed to in attempts to avoid these effects to certain degrees. Thus, Wallace, in U.S. Pat. No. 2,350,378 and Morrow, in U.S. Pat. No. 3,413,199, disclose including some abrasive mechanism in the flow cell to keep the anode clean and electrically active. The difficulty with use of an abrasive, however, is that the abrasive nature of the cleaning wears away electrode material. The abrasive material also needs periodic addition or replacement and can require a tedious process of disassembling the flow cell.

Other techniques for protecting the integrity of the electrodes use a membrane-covered anode or a membrane covering both the anode and the cathode and enclosing them in an electrolytic solution. The membrane is permeable to the chemical that is the subject of the measurement, allowing the chemical to pass through the membrane and, due to the combination of the bias voltage and electrolyte, is reduced at the cathode.

These arrangements, however, also suffer from several drawbacks. For instance, they require periodic refilling of the electrolyte solution within the membrane and sometimes complete disassembly to replace the membrane or for other cleaning and maintenance. Moreover, as with the galvanic sensor, measurement also sometimes requires pH-buffering to stabilize and or to reduce the pH of the water to be tested to a certain level.

Other types of chlorine electrodes have been fabricated without membranes, but they require a buffer solution to adjust the pH to a set value for the measurement to be valid. One such arrangement, discussed by Nakagawa in U.S. Pat. No. 3,902,982, uses bare electrodes housed in a chamber that is fixed to a motor that stirs, at a fixed rate, the solution to which is added a buffer solution. This system not only uses a buffer but requires a sample to be taken at various times precluding its use in any inline monitoring application. Morrow, in U.S. Pat. No. 3,959,087, teaches an electrode assembly wherein both electrodes comprise copper and wherein a buffer solution is not required between pH 5 and pH 9. In practice, however, this arrangement has been found to be very susceptible to the amount of chloride-based salt in the water. Many pools in use today use chlorine that is generated on site by sodium chloride salt added to the water which is converted to chlorine through an electrolytic cell. The conductivity in these systems is quite high, such as about 6000 μS or about 3000 ppm. In addition, this arrangement has been found to exhibit random steps in the electrical response to the addition of chlorine or when fresh water is added to the system.

Still other methods involve using electrical pulses of various levels and polarity to de-plate contaminants from the electrode surface. These methods are based on the specific contaminants that are to be removed. Outside of a laboratory setting with known contaminants, the effects of electrical cleaning can be random and even detrimental to the measuring process. Considering the wide range of possible contaminants in pool water, therefore, this method is not practical.

Corrosion resistance and catalytic activity considerations for the anode of the sensing cell are somewhat differently than they are for the cathode. The anode functions primarily to supply electrons in the reduction of chlorine at the cathode. As such, the primary requirements with regard to the anode are electroactivity and corrosion resistance. The cathode, in contrast, is where the chlorine is reduced, and noble metals are more catalytically active in this regard. However, although noble metals are quite corrosion resistant, corrosion resistance is not the ultimate criterion for selecting a cathodic material. For example, titanium is among the most non corrosive metals known but it passivates quickly, almost completely eliminating any current flow.

For those sensors in which a bias voltage is applied, the bias voltage chosen is based on the oxidizing or reducing potential of the chemical of measurement. The sensor signal exhibits a plateau of limited current at the characteristic reduction potential of the element. In addition, the diffusion is rate limited because, at the reduction potential, the entire amount of oxidizer present is reduced at the cathode. However, in water environments common to pools and spas, the conditions for diffusion limited current are not very favorable, as noted by Marks and Bannister in *Amperometric Methods in the Control of Water Chlorination*, Analytical Chemistry, Vol. 19, No. 3, pp. 200-204 (1947). However, as noticed by Marks and Bannister, even though there is not necessarily a diffusion limited current, the current still maintains a linear relationship to the level of chlorine based on the applied bias voltage and the concentration of oxidizing compound in the normal range of oxidizer residuals.

With respect to pH sensors, many of those known in the prior art are based on the H+ sensitivity of certain microporous glass mixtures. The glass is highly selective toward H+ ions and responds quickly to changes in pH. The sensing portion of the sensor is usually mounted in a common housing that also contains a reference electrode. The reference electrode provides a stable electrochemical interface to the test solution and completes the electrical circuit providing the signal.

The reference electrode typically contains an equilibrium mixture of sodium or potassium chloride, silver chloride and a silver wire that has a coating of silver chloride. The reference electrode is coupled electrolytically to the sensing portion by a porous junction, typically of microporous Teflon®. The electrolytic coupling is maintained by a small leakage of the internal fill solution through the porous junction to the solution being measured.

Such electrodes suffer from several drawbacks. The glass-sensing portion is of extremely high impedance, typically on the order of 100-500 megohms, thus requiring a very high input impedance amplifier to measure the signal properly. The reference electrode also has impedance associated with it, based on the leak rate of the internal fill solution. Therefore, the reference electrode must provide a sufficient leak rate to minimize the impact on the total electrode impedance. The leak rate of the reference electrode, however, directly effects the lifetime of the sensor. The high input impedance also makes the system very susceptible to noise and grounding problems. In addition, the electrodes are quite delicate due to the fragile nature of H+ sensitive glass, which also is very susceptible to fouling by organic contaminants, especially those found in pools. Such sensors also are quite expensive and have a relatively short life, especially in inline systems exposed to constant flow. More rugged versions of the probes are available that attempt to protect the glass sensing surface and contain larger amounts of internal fill solution, but this adds even further to the cost.

Other pH sensors of various sensing mechanisms are also known. For example, some sensors are based on ionically sensitive field effect transistors (ISFET). The gate of the transistor is coated with a pH sensitive polymer. The transistor is biased in such a way that when the gate is exposed to changing pH, a voltage change on the circuit output is caused. The main difficulty with these sensors is they require a specific meter that is calibrated for each sensor. Further, these sensors are extremely expensive, which has limited their widespread acceptance.

Other pH sensors are based on various pH-sensitive polymers coated onto an electrical substrate. Such sensors are used mainly in a laboratory environment and have an extremely short lifespan in a pool environment due to incompatibilities of the polymer coatings with the chemicals used to treat the water.

Antimony pH electrodes also are known in the prior art. Antimony pH sensors employ a piece of monocrystalline antimony because it has been known to have a more reproducible pH response. See, for example, U.S. Pat. No. 4,119,498 to Edwall et al. However, such sensors have been found to suffer particular drawbacks when applied to swimming pool measurements. For instance, since the antimony electrodes are composed of crystaligraphically-oriented antimony, they are very small and flat with almost a mirror-like surface. This small size results in a relatively high electrical impedance and very rapid oxidation in even mild oxidizing environments. The mirror surface also does not lend itself to any sort of protective coating due to problems with adhesion.

Other antimony pH sensors use polycrystalline rod material with various methods used to seal the interface between the antimony and the sensor housing (see U.S. Pat. No. 4,681,116 to Settler, and U.S. Pat. No. 3,742,594 to Kleinberg). However, these electrodes do not address the oxidation issues and also suffer from all the attendant difficulties associated with bare antimony.

The subject inventor's U.S. Pat. No. 6,653,842 described a pH sensor based on an antimony/antimony oxide electrode. The reference electrode of that patent was a bare metal electrode as described therein. The pH sensor of that patent was based on the galvanic potential between the antimony and metal reference electrode. In water at relatively low levels of chlorine (less than 3 ppm), the electrode is minimally affected by the presence of the chlorine, but at levels above that, the oxidizing effects of the chlorine start to modify the electrode surface of both the antimony and the metal reference electrode. Surface scans of the electrodes show that that the largest part is composed of antimony of several electron states as well as the effect of high chlorine (5 ppm) on the antimony. From the photomicrographs and scans, it can be seen that, after exposure to a high chlorine environment, the surface of the antimony has less pure antimony than it had originally and the relative amounts of carbon and oxygen have increased. Also as can be seen from EDA scans of the zinc reference electrode, the antimony has been deposited on its surface. The effect of this plating is to reduce the galvanic potential between the antimony and zinc, causing a shift in signal offset and a reduction in sensitivity to pH changes. The sensors, therefore, require abrasive cleaning before the response returns to normal. Since abrasive cleaning techniques are not suitable for consumer use, this electrode would not be suitable for long-term measurement systems where the chlorine concentration is high (above about 2 ppm).

Various solutions have been proposed to address the problem of electrode erosion and degradation. For example, U.S. Pat. No. 4,818,365 to Kinlen proposes using dip coatings of Nafion. The methods of Kinlen, wherein he dip coated electrodes in a Nafion solution and cured and then annealed them, was investigated. It was found with respect to antimony that the coatings resulting from this process were not only highly variable regarding their pH response but also retained insufficient adhesion and uniformity to the metal surface.

A major difficulty in using dipped and cured coatings of Nafion on antimony is that the curing process has a difficult process endpoint based on time in the oven and its temperature as noted by Kinlen. In other words, insufficient heat or time or too much heat or time in the oven has been found to have dramatic effects on the resultant coatings.

An additional difficulty in pH sensing is that the degree of adhesion of the coating to the electrode greatly affects the relative sensitivity of the electrode with respect to pH changes. This aspect of adhesion regarding sensitivity was not as pronounced with the chlorine sensor in that the primary requirement of the anode was to supply electrons wherein the electrical resistivity was the principal issue. In the case of the pH electrode the principal issue is the sensitivity to hydrogen. Nafion acts as a barrier to chlorine while allowing hydrogen to pass through. However there exists an impedance gradient between the inside surface of the membrane and the metal surface with regard to hydrogen sensitivity. Depending on the degree of adhesion this gradient is highly variable resulting in a range of sensitivities that are fairly random. Also affecting the sensitivity is the thickness of the membrane; the thicker the membrane the higher the resistance to the passage of hydrogen ions. Photomicrographs of a Nafion dip coating have shown the difference in coating thickness on different areas of the same antimony electrode. The electrode surface showed a blistered appearance after a time in water. This difficulty was also referred to regarding the chlorine anode earlier.

Mosier et al patent application Ser. No. 10/848,196 teaches a method of using Nafion tubing around a platinum anode coupled with a porous titanium cathode with a Nafion membrane over the end exposed to water. The electrodes then are subjected to an extremely high voltage (~1500V) and used to drive an Electro Kinetic pump. The driving force electrolizes the water between the electrodes that generate hydraulic pressure and in the process produce air bubbles that limit long term stabile operation of the pumps. Therefore, to eliminate the gas bubbles generated during electrolysis, Mosier et al. provide and air vent at the end of the anode exposed to air. The exposure of the anode to oxygen is detrimental to the long term functioning of the electrode used in sensing an amperometric parameter as in chlorine/bromine measurement.

Sensors for measuring the total dissolved solids (TDS) in water are used to measure the amount of dissolved salt in pool and spa environments, as well as in many other aqueous environments. TDS is related to the conductivity of the water and is a useful measurement in that there are guidelines related to the maximum amount of dissolved solids that are allowed in drinking water and in pool/spa environments. In addition, certain conditions in a swimming environment are sometimes difficult to diagnose without knowing its TDS level. TDS also can interfere with the effectiveness of the sanitizer, allowing algae formation even when the sanitizer is at the recommended level. Moreover, chlorine is generated on site for pools that use dissolved salts in the water. In such cases measurement of TDS is needed because the chlorine generators require a minimum amount of dissolved in the form of salt in the water for the chlorine generator to function properly. However, generally, the instrumentation to measure TDS is based on special test strips or costly meters and probes.

Thus, there is a clear need in the marketplace for an efficient low cost reliable long-term measurement system for measuring pH, halide (e.g., Cl or Br) concentration, temperature and total dissolved solids (TDS) to allow wider usage in smaller residential pools and spas as well as in commercial pools or other high end residential applications and, in particular, a such a system that eliminates the need for frequent cleaning.

SUMMARY OF THE INVENTION

Briefly, therefore, the present invention is directed to a novel reference electrode assembly comprising a reference electrode in contact with a halide-saturated gel. The electrode and gel are enclosed within a non-conductive, waterproof container having a water-porous but not gel-porous, ion exchange interface.

In another embodiment, the invention is directed to a reference electrode assembly comprising a reference electrode in a non-conductive, waterproof container of a halide-saturated gel. The electrode is thereby in contact with the gel in the container and the waterproof container has a water-porous but not gel-porous, ion exchange interface.

In yet another embodiment, the invention is directed to an electrolytic combination comprising a reference electrode assembly in a bath. The assembly comprises a reference electrode in contact with a halide-saturated gel. The electrode and gel are enclosed within a non-conductive, waterproof container having a water-porous but not gel-porous, ion exchange interface that provides electrolytic communication between the gel and the bath.

In still another embodiment, the invention is directed to a halogen sensor comprising a metal anode shielded by a low electrical resistance, water-permeable, oxygen barrier of at least about 0.004 inches in thickness, and a metal cathode.

In still another embodiment, the invention is directed to an electrolytic combination comprising a reference electrode assembly in a water sample. The assembly comprises a reference electrode in contact with a halide-saturated gel. The electrode and gel are enclosed within a non-conductive, waterproof container having a water-porous but not gel-porous, ion exchange interface that provides electrolytic communication between the gel and the water sample.

In still another embodiment, the invention is directed to a halogen sensor comprising a metal anode shielded by a low electrical resistance, water-permeable, oxygen barrier of at least about 0.004 inches in thickness, and a metal cathode.

In still another embodiment, the invention is directed to a pH-sensor comprising an anode of a bare noble metal having an electroactive surface and a cathode of a noble metal having an electroactive surface sealed within a Nafion tube such as to prevent exposure of the cathode to ambient oxygen from the environment exterior to the tube, except as may pass through the tube.

In still another embodiment, the invention is directed to a pH sensor comprising a pH-sensitive material encased in a Nafion tube such as to prevent exposure of the cathode to ambient oxygen from the environment exterior to the tube, except as may pass through the tube.

In still another embodiment, the invention is directed to a total dissolved sensor (TDS) comprising:
- a pair of spaced-apart electrodes excited by a sine wave voltage;
- a current amplifier and rectifier electrically responsive to the pair of spaced-apart electrodes to generate a voltage indicative of the voltage between the spaced-apart electrodes;
- a converter electrically responsive to the voltage indicative of the voltage between the spaced-apart electrodes to convert the indicative voltage for at least one of display and processing;
- a display electrically responsive to the converter to display a total dissolved solids measurement in water in which the pair of spaced apart electrodes is placed.

In still another embodiment, the invention is directed to a method for measuring an amount of total dissolved solids in water, the method comprising:
- exciting a pair of spaced-apart electrodes with a sine wave;
- amplifying and rectifying a current from the spaced-apart electrodes to generate a voltage indicative of the voltage between the spaced-apart electrodes;
- converting the voltage indicative of the voltage between the spaced-apart electrodes for at least one of display and processing; and
- displaying a total dissolved solids measurement utilizing an output of the converter.

BRIEF DESCRIPTION OF THE DRAWINGS

FIG. PA-1 is a graph showing prior art ORP response versus the level of active chlorine in a water sample.

FIG. PA-2 is a graph showing the current response versus chlorine level for a prior art galvanic sensor in a water sample.

Corresponding reference numbers indicate corresponding parts throughout the several views of the drawings.

DETAILED DESCRIPTION OF THE PREFERRED EMBODIMENTS

In accordance with the present invention, it has been discovered that, surprisingly, a relatively low-cost, durable, long-lasting and accurate measurement configuration comprising a probe or group of probes capable of measuring pH, halogen in parts per million (ppm), temperature, and total dissolved solids (TDS) in ppm in aqueous liquid environments even in high chlorine environments such as swimming pools and spas can be produced as described below.

The components of the configuration include a reference electrode, a halogen sensor, a TDS sensor, a pH sensor and a temperature sensor. Each of the components—the reference electrode, halogen sensor, TDS sensor, and pH sensor—are believed to be novel and may be used in combination with conventional components or with one or more of the other novel components of this invention. Such components can be housed together or separately, as will be discussed below.

Reference Electrode

In accordance with the present invention, it has been discovered that, surprisingly, a reference electrode assembly comprising a reference electrode in contact with a halide-saturated gel within a non-conductive, waterproof container having a water-porous but not gel-porous, ion exchange interface allows electrolytic contact between the gel and the environment being tested, yet resists leakage of the gel into the environment, can be made from materials far less fragile than glass, and allows the reference electrode assembly to be employed in orientations beyond just vertical. In fact, it has been found that the leak rate in this new electrode assembly is so low that it may be employed for several months or more without service or replacement.

Figure 1:
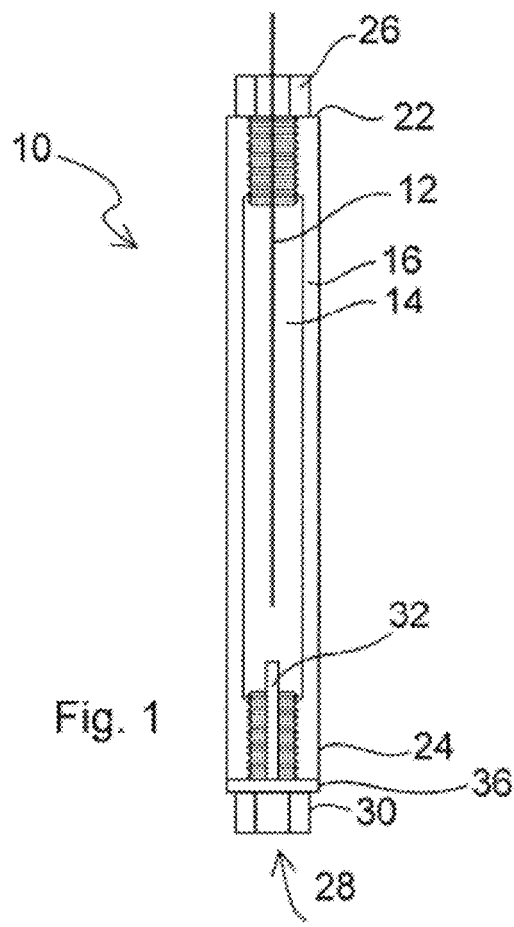
FIG. 1 is a schematic representation of a reference electrode assembly of the present invention.

As shown in FIG. 1, the electrode assembly 10 comprises an electrode 12 in a gel 14 within a container 16. Preferably, the container 16 is formed of a rigid material that is inert with respect to the environment to be tested (the "sensing" or "test" environment) and the gel 14, and non-electrically conductive. By "inert with respect to" such environment and gel, what is meant is that it is not affected deleteriously by the environment or gel and does not react or interact with the environment or gel such as to interfere with the measurements carried out or to be carried out with the electrode assembly. For example, for an aqueous test environment such as pool or spa water, the container 16 should be formed or a material that is non-rusting or at least rust-resistant. Moreover, the container 16 should be non-electrically conductive. As used herein, by "non-electrically conductive" what is meant that the container is not electrically conductive to a degree such as to interfere with the measurements made or to be made with the reference electrode. In addition, it is also desirable for the container 16 not to be of a fragile material such as glass. Thus, an example of a preferred material is rigid plastic such as rigid PVC.

In the embodiment shown in FIG. 1, the container 16 is a tube having opposite ends 22 and 24. The electrode 12 extends inwardly through the end 22. The end 22 is capped with a seal against leakage of the test environment into the container 16 and against leakage of the gel 14 out of the container 16. Generally, therefore, electrode 12 extends through a watertight seal 26 at end 22. While a preferred embodiment contemplates that the electrode 12 extends through the watertight seal 26, with the opening in watertight seal 26 through which the electrode 12 extends sufficiently sealed to or against the electrode 12 to prevent water leakage therethrough, it should be understood that other techniques may be employed to avoid breaking a watertight seal at end 22 of container 16. For example, watertight seal 26 may have an electrical contact accessible from the interior of container 26, the electrical contact being in electrical communication with a terminal outside container 26, such on a portion of watertight seal 26 outside container 16, and the electrode may abut the electrical contact of watertight seal 26.

At the opposite end 24 of the container 16, an ion exchange assembly 28 provides electrolytic communication between the gel 14 and the test environment outside the container 16, but inhibits or prevents leakage of the gel 14 from the container 16 to the test environment. This ion exchange assembly is similar to those described in U.S. Pat. Nos. 3,298,944 and 3,790,463, incorporated herein by reference, and identified in the former patent as electrolytic bridge assembly 18 and illustrated in the latter patent in various embodiments shown in the lower portions of each of the figures thereof.

Figure 2A:
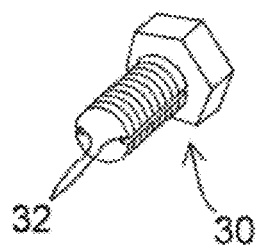
FIG. 2a is a perspective view of a bolt employed in a preferred embodiment of the reference electrode assembly of the present invention.
Figure 2B:
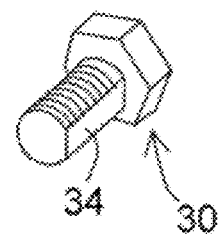
FIG. 2b is a perspective view of another embodiment of a bolt employed in a preferred embodiment of the reference electrode assembly of the present invention.

In the embodiment shown in FIG. 1, the ion exchange assembly 28 comprises a threaded bolt 30, as illustrated also in FIGS. 2a and 2b. The bolt 30 comprises a longitudinal channel or channels. FIGS. 2a and 2b show two alternative configurations of the channel(s). As shown in FIG. 2a, the channel(s) may be one or more longitudinal grooves or slits 32. As shown in FIG. 2b, the channel(s) may be a bevel 34.

Mounted on the bolt 30 and situated against the head of the bolt 30 in the electrode assembly 10 of FIG. 1 is an electrolytic bridge material in the form of a porous washer 36 such as of cellulose fiber. The washer 36 is formed of a porous material in the sense that it absorbs some of the electrolytic gel 14 (which may be by absorbing a portion of some component of the gel, such as a portion of the solvent or some portion of the solvent and some solute) or some of the environment surrounding the electrode assembly 10 (in particular some portion of the test environment), or both. Preferably, the washer material is a cellulose fiber material, such as one capable of absorbing more than 50% of its weight in water, such as about 66% of its weight in water. Such high degree of absorption not only provides an effective ionic bridge, but tends to swell the washer, providing a better barrier against leakage of fluid in or out of the electrode assembly 10. Thus, the electrolytic bridge material is sufficiently porous to allow ion exchange therethrough yet, as will be discussed further below, prevents or is substantially resistant to leakage of the gelled electrolyte in the electrode assembly.

The interior of container end 24 is threaded in complement to the threaded stem of the bolt so as to receive and to engage bolt 30 so that by turning the bolt 30, bolt 30 may be tightened against the container end 24, with the washer 36 sandwiched between the head of the bolt 30 and the container end 24 and the bolt 30 is thereby held frictionally in threaded engagement with the container 16. Thus, tightening the bolt 30 increases the squeezing or sandwiching pressure applied to the washer 36 and the circumferential edge of the washer is exposed to the environment about the electrode assembly 10. It has been found that tightening the bolt until a resistance across the electrode assembly is under about 1,000 ohms is sufficient to provide sufficient ion exchange without undesirably high leakage in or out of the electrode assembly.

Figure 3:
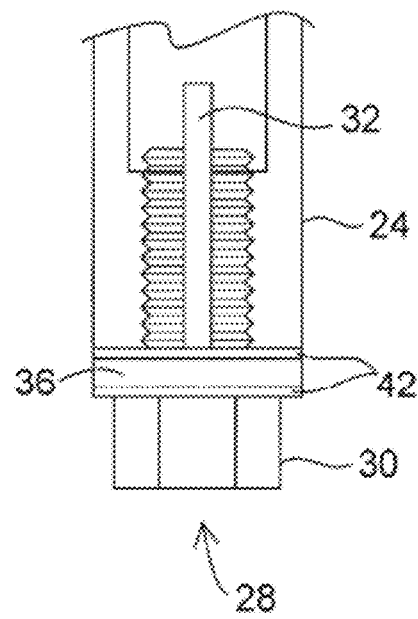
FIG. 3 is a partial schematic representation of a second embodiment of a reference electrode assembly of the present invention.

The channel(s) of the bolt 30 thereby extend(s) from the bulk of the electrolytic gel 14 in the container 16 to the washer 36, allowing the gel 14 to flow into the channel(s) to the washer 16 so that the electrolytic gel 14 is in electrolytic communication with the washer 36 and thereby also the environment about the electrode assembly 10 via the washer 36, which absorbs some of the electrolytic gel 14, the test environment about the electrode assembly 10 or both. If so desired and as illustrated in FIG. 3, a pair of low friction washers 42, such as nylon washers, may be included on the opposite sides of the washer 36 so as to sandwich the washer 36 between the washers 42 and allowing greater pressure to be applied to the washer 36 without tearing it.

As thus configured, the ion exchange assembly 28 provides a watertight seal at the container end 24, except for a passageway that permits ion exchange and therefore electrolytic communication between the electrolytic gel 14 in the container 16 and the exterior test environment, the passageway comprising the longitudinal channel(s) of the bolt 30 in combination with the porous washer 36.

It has been found that cellulose fiber washers capable of absorbing water up to at least about 50%, such as about 66%, of its dry weight are particularly suitable. In fact, it has been found that use of washers of such high water-absorptivity result in an ionic bridge that is not significantly affected by the differences in thermal expansion coefficients that were of concern in U.S. Pat. No. 3,790,463. Moreover, it also has been found that a sufficient ionic bridge in the subject assembly can be maintained even when the bolt 30 is tightened sufficiently to eliminate or at least greatly reduce the leakage that was of concern in U.S. Pat. No. 3,298,944.

While elimination of leakage is preferred, it is recognized that extremely slow leakage is possible while still providing a superior electrode assembly. Accordingly, when near prevention or elimination of leakage is discussed herein, it should be understood that what is meant is that in the electrode assembly of this invention, there is either no leakage or at least very little leakage relative to what was experienced in prior art devices. Thus, the leakage is sufficiently low that the life of the electrode assembly under ordinary test conditions is at least two months.

In a preferred embodiment, the electrode 12 is a halide-coated noble metal. Preferably, the noble metal is of high purity, such as at least about 99.99% by weight. Also, preferably, the halide coating is a halide salt, particularly a salt of the noble metal, and is in electrochemical contact with the noble metal—especially, in direct contact thereto. Most preferably, the halide is a chloride salt and the electrode is chloride-coated silver, especially silver chloride-coated high purity silver. In an especially preferred embodiment, the silver is of at least about 99.99% by weight pure. The electrode may be of any standard shape and the metal may be overlaid on a substrate such as a polymeric support, with the exposed metal surface coated with the halide. For example, U.S. Pat. No. 4,199,412 teaches that the silver-silver halide electrode can be produced by vacuum-depositing silver onto an insulating polymeric film or other suitable support and then chemically converting the exposed surface the silver layer to silver halide. Preferably, however, the electrode comprises solely the noble metal and the halide in electrochemical contact thereto.

Thus, an especially desired form of the electrode 12 is a wire of high purity silver that has been chloride coated, such as by known electrochemical or other methods. One particularly suitable technique for chloride-coating the silver wire is to soak it in a chlorine solution for about eight hours or more. Other coating methods, however, are well known in the art. For example, U.S. Pat. No. 4,199,412 teaches dipping the silver into a solution of molten silver halide.

The halide-coated metal may be used in the electrode assembly in that form. However, it has been found that the halide coating tends to strip away during use. Therefore, preferably, the halide-coated metal is coated with an ion-permeable, more preferably a halide ion-permeable, especially a chloride ion-permeable, barrier to inhibit the stripping away of the halide coating from the electrode.

Previous patentees have described or alluded to various techniques for applying an ion-permeable barrier to an electrode. For example, U.S. Pat. No. 3,591,482 describes a method of coating the halide layer (in that patent and preferably in the present device, a silver chloride layer) with a thin layer of methyl methacrylate of about 25 microns in thickness by dipping the halide-coated metal into "molten methacrylate" to form a coating that still "allows the silver chloride surface to retain its chloride ion sensitivity." While the '482 patent refers to methacrylate, with special attention to methyl methacrylate, it notes explicitly that other methacrylates, such as ethyl or butyl methacrylate, may be employed.

U.S. Pat. No. 4,199,412 describes a method for applying an ion-permeable layer to a metal/metal halide electrode to form an ion-selective overlayer to allow passage of ions of interest while inhibiting the effect of interfering ions. That patent recognizes that the specific method of application of the overlayer depends on the physical shape of the underlying electrode, and notes that when the electrode is a wire electrode (as is preferred in the present invention), the simplest method for applying the overlayer may be dipping or spraying. The patentees report that they generally apply their overlayer by forming a solution of the constituent composition of the overlayer in a suitable solvent, applying the solution to the electrode, and then driving off the solvent under drying conditions.

U.S. Pat. No. 5,213,675 describes a reference electrode bearing a laminated protective coating over a silver/silver halide electrode. The laminated coating is formed by alternately laminating salt layers and hydrophobic resin layers. While the first layer is a silver halide layer, one or more of the other salt layers may contain a salt other than the silver halide, such as potassium chloride, sodium chloride, ammonium chloride, lithium chloride, other halide salts, or even non-halide salts such as sodium nitrate and sodium sulfate.

In the electrode of the '675 patent, it is stated that the hydrophobic resin may be any resin having hydrophobicity, such as polyolefin, polystyrene, polyimide, polycarbonate, polymethyl-methacrylate (PMMA), polytetrafluoroethylene, polyvinyl fluoride, polyvinylidene fluoride and other fluorine resins, but polytetrafluoroethylene is identified as particularly suitable. And according to the '675 patent, the halide salt layers and the like are formed by techniques such as a vacuum deposition process, a sputtering process, an ion plating process, or a cluster ion beam process, while the hydrophobic resin layers are formed by a CVD (chemical vapor deposition) process, an ion plating process, a cluster ion beam process, a plasma polymerization process, a sputtering process, a photoresist process, or the like.

In the present invention, it has been found that an effective ion-permeable may be applied by the following procedures. In these descriptions, the electrode will be referred to simply as a silver wire, although it should be understood that in accordance with the above description of the electrode, the wire is coated with a halide such as silver chloride and other electrode configurations and metals may be employed in place of the silver wire.

Most desirably, the coating is water-insoluble. For example, the coating may be a laminate of methacrylate, PVC or other water-insoluble material impregnated with a salt, such as by forming a first layer of the water-insoluble material over the silver halide on the surface of the silver wire, a layer of salt over that first layer of water-insoluble material, and one or more layers of the water-insoluble material over the salt layer.

When the coating is a methacrylate, preferably a lower (C1-4₇) alkyl methacrylate, such as methyl methacrylate, the silver wire may be dipped in a bath of the methacrylate. Although the methacrylate is a liquid in the bath, it reacts quickly with the ambient oxygen in the air and solidifies on the wire. The methacrylate-coated wire is then dipped and thus coated in a salt. The salt is preferably a halide salt, more preferably a chloride salt such as sodium chloride or potassium chloride, in granular or powder form. The salt coated electrode is then dipped in the methacrylate bath, and may be subject a series of alternating dipping and drying steps until a coating on the order of about 2 mils (about 50 microns) is formed.

Alternatively, a bath of PVC glue may be used in place of the methacrylate bath. The bath of PVC glue may be prepared by dissolving powdered PVC in an organic solvent. The silver wire may be dip-coated in the PVC glue bath, dried by evaporation of the solvent, dipped in the salt and then re-coated several times with the PVC glue (with drying steps interspersed between the dips) to form a total coating of about 2 mils (about 50 microns) over the metal halide on the wire.

Thus, in both cases, the resulting ion-permeable barrier is impregnated with the salt, creating a water-insoluble, electrically conductive protective coating.

The electrolytic gel 14 is a gelled saturated chloride solution, preferably a gelled solution saturated with sodium chloride, potassium chloride or both. It may be prepared by first preparing a saturated aqueous solution of sodium chloride, potassium chloride or both and then adding a gelling agent to the saturated solution. It is preferred that the saturated solution be prepared prior to addition of the gelling agent because it has been found that the gelling agent tends to reduce the solubility of the chloride salt, resulting in a lower concentration of the chloride salt. Standard gelling agents, such as hydroxyethyl cellulose, may be employed. In particular, METHOCEL™ cellulose ethers, which are water-soluble methylcellulose and hydroxypropyl methylcellulose polymers available from Dow Chemical Company, have been found to be acceptable gelling agents.

A small amount of silver chloride, but sufficient to ensure an excess beyond saturation, is then added to the gel to saturate the gel with silver chloride. It has been found that such saturation inhibits chloride loss from the electrode in the gel.

The electrode assembly thus formed has been found to yield surprising accurate results in combination with test electrodes for surprisingly long periods of time; generally on the order of months or more. In addition, because the electrode assembly does not include fragile materials such as glass, it is relatively rugged compared with conventional reference electrode assemblies. Moreover, because it is fluid tight (except for the relatively minor flow, if any, through the ion exchange membrane) and does not contain a liquid that is oriented in the electrode assembly depending on the spatial orientation of the assembly, the electrode assembly may be mounted in any orientation in a test environment.

The reference electrode assembly therefore may be employed in a bath. By bath, what is meant is any liquid environment that allows electrolytic communication between the reference electrode assembly and a paired electrode also in the bath. Thus, the combination is suitable for electrolytic application or measurement. Normally, the bath would be aqueous such as an aqueous solution, especially a pool or spa. Typically, the reference electrode assembly would be paired with another electrode, such as a test electrode, such that the two are in electrolytic communication via the bath.

Halogen Sensor

Figure 4:
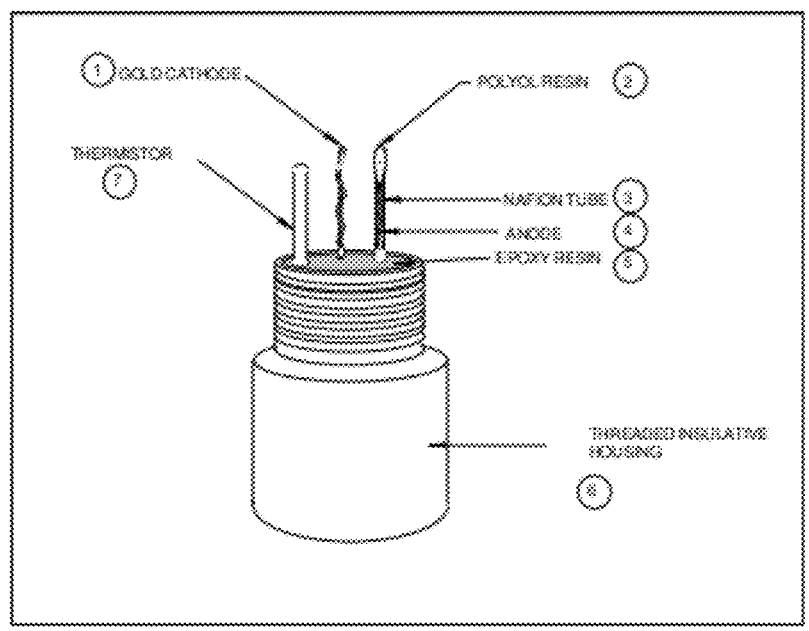
FIG. 4 is a perspective view of an embodiment of a halogen sensor of the present invention.

The chlorine sensor of the present invention is an improved amperometric sensor that allows chlorine to be measured in parts per million using and extends the range of measurement beyond the capabilities of current ORP type measurements in pools and spas. An embodiment of the halogen sensor of the present invention is illustrated in FIG. 4. The halogen sensing electrode comprises a cathode of a bare noble metal having an electroactive surface (that is, the metal surface reacts sufficiently to specific chemicals or conditions of interest that it provides a measurable indication of the level of activity thereof) and an anode of a noble metal having an electroactive surface disposed inside a Nafion tube and sealed at both ends so as to prevent exposure of the anode to the environment, except as elements of the environment may pass through the tube, and particularly to prevent exposure of the anode to ambient oxygen from the environment exterior to the tube, except as may pass through the tube.

Optionally, a temperature sensor is mounted in close proximity to the anode/cathode pair to sense temperature around the electrodes for adjustments for adjustments that may be necessary for accurate readings based on temperature. A bias voltage is applied between the electrodes, positive to the anode and negative applied to the cathode, with an approximate level of the reduction potential at the cathode for the halogen to be sensed while minimizing $O_2$ reduction at the cathode; about 1V for chlorine. The result is a current that is proportional to a range of concentrations of electroactive species without necessitating a limiting current.

An anode may be used as a halogen sensor in combination with a cathodic reference electrode. As noted above, prior art anodes have tended to suffer from a lack of durability. The anode durability of the present invention is achieved by placing it inside a small diameter thin-walled tube 3 of oxygen and anion impermeable, tubing. There are different kinds of membranes that are relatively impervious to various ions and oxygen, although such relatively ion and oxygen impermeable materials still have a finite ability to pass a very small amount of oxygen and some other ions. Nafion is one such relatively oxygen-impermeable, ion exchange polymer, along with other perfluorosulfinated polymers of various formulations. Nafion such as produced by du Pont and manufactured by Perma Pure LLC is a particular embodiment found useful in the present invention. Nafion and such polymers may be used for halogen sensors to provide a barrier to oxygen and negatively charges anions such as chlorine. Although, as mentioned previously, such polymers pass minute amounts of oxygen it has been found that with regard to precluding oxidation of the anode in such halogen sensors they function well.

While the wall should be thick enough to protect the anode, it should not be so thick as to prevent sufficient ion-permeability. Surprisingly, it has been found to be possible to accommodate such contradictory considerations. For example, for Nafion tubing, a wall thickness of approximately 0.004 to 0.006 inches has been found to be appropriate to balance those considerations.

Such Nafion tubes are manufactured by Perma Pure LLC under very reproducible processes and are highly uniform in consistency. Nafion is a poly(tetrafluoroethylene) polymer that contains sulfonic and carboxylic acid groups and is very resistant to chemical attack. The polymer is therefore highly negatively charged and its pore structure makes it possible to use the membrane as a cation-selective barrier. In particular, Nafion is a proton exhange membrane, As such, it will permit the difussion of small cations such as $H^+$ and repel negative charged anions such as $Cl^-$. Nafion will also readily accept electrons which enhances its electronic conductivity and its use as a catalyst in processes requiring the removal of electrons to initiate the reaction. In practice, the membrane is permeable only to relatively small amounts of oxygen. It can be converted to other salt forms by known methods such as through sufficient exposure to large concentrations of other ions such as sodium, potassium, lithium, and so forth but as a matter of exposure in a pool/spa environment, the hydrogen permeation and electron acceptance and the relative impermeability of $O_2$ and $Cl^-$ is the predominant factor in the electrode response.

Moreover, the tubing is water-permeable, gas impermeable. It should be appreciated, however, that while the pH sensor discussed above employs Nafion tubing as well, the membrane specific to amperometric halogen sensing, as opposed to pH sensing discussed above, has the primary function of preventing oxidation of the anode as opposed to preventing the transfer of negatively charged chlorine anions required for the antimony pH sensor.

Particularly suitable Perma Pure Nafion tubes have been found to be Model Number TT-030, which has an inner diameter of 0.025 inches, and outer diameter of 0.033 inches and a wall thickness of 0.004 inches, Model Number TT-050, which has an inner diameter of 0.042 inches, and outer diameter of 0.053 inches and a wall thickness of 0.005 inches, Model Number TT-060, which has an inner diameter of 0.052 inches, and outer diameter of 0.063 inches and a wall thickness of 0.006 inches and Model Number TT-070, which has an inner diameter of 0.060 inches, and outer diameter of 0.072 inches and a wall thickness of 0.006 inches.

Although prior attempts at Nafion protection of the anode involved dip-coating the anode with liquid Nafion that is then cured, as discussed in the Kinlen references noted above, sections of the thus-prepared Nafion coatings were found to peel or to break off during extended use. Accordingly, such attempts did not provide satisfactory protection. However, adhesion to the electrode surface is not an issue with the tube-form of Nafion.

Figure 6:
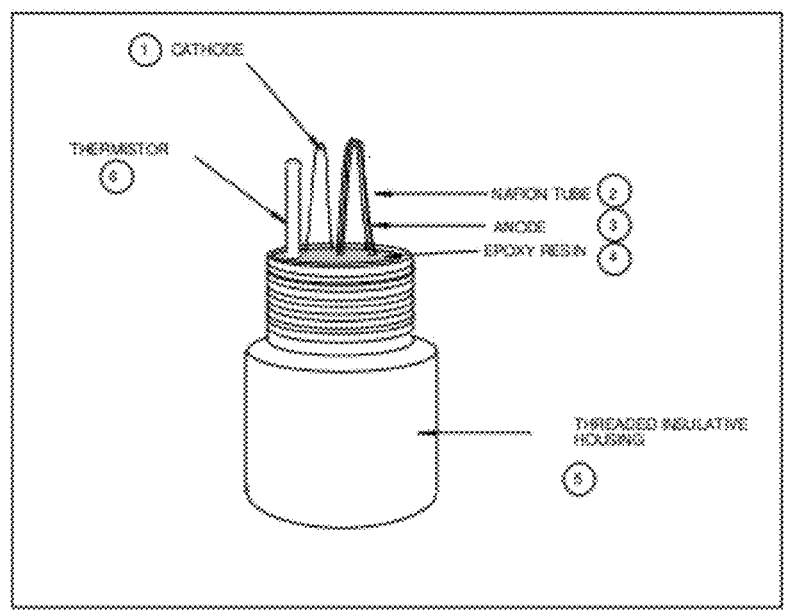
FIG. 6 is a perspective view of a second embodiment of the halogen sensor.

It has been found that the electrical impedance of the anode is a function of the proximity of the inner wall of the tube to the metal surface; that the closer the inner wall is to the surface of the electrode, the lower the impedance of the electrode. Therefore, the inner diameter of the tubing preferably is selected so that the fit of the anode within tubing is tight, resulting in the inner wall of the tubing being very close to the exterior surface of the anode and most preferably as close as possible to the anode. The Nafion tube may also be of a smaller diameter than the electrode and wetted to enlarge it sufficiently to fit over the electrode also providing a very snug fit. The anode may be sealed within the tube by various techniques. For example, the tip of the anode and tube may be sealed with a polyol resin 2 as shown in FIG. 4. Alternatively, the Nafion tube and the anode encased in the Nafion tube can be bent in a U-shape (or V-shape, etc.) so that both ends may be implanted in the material in which the anode is seated and from which it extends, as shown in FIG. 6. The bare cathode likewise may be bent in a U-shape (or V-shape, etc.) so that both ends may be implanted in the material in which the anode is seated and from which it extends. While the shapes of the electrodes are described as U-shaped or V-shaped, it will be understood that any of a number of shapes may be employed, the key feature of the shape being that the opposite ends extend into a part that seals them. Preferably, both ends of both electrodes (and ends of the tubes in which they are encased) are potted in a resin sealant such as that manufactured by Reltek LLC as BONDiT-BT45TH. In this manner both ends of the Nafion tube of both electrodes are sealed. The BONDiT-B45TH resin is specially formulated to adhere to surfaces such as PTFE (Teflon), which is a significant component of Nafion.

Moreover, because the Nafion tube is oxygen-impermeable, it nearly eliminates corrosion of the anode. Therefore, the platinum wire of prior art anodes may be replaced by a stainless steel pin, thereby lowering the cost of the electrode. In addition, a pin is much more rigid than platinum wire and can be produced in a diameter to fit the inner diameter of the Nafion tube closely, allowing for lower electrical impedance as well as reducing the cost of the electrode. For additional cost savings, it has been found that the platinum used for the cathode 1 may be replaced with gold.

Also, because the halogen measurement is also sensitive to temperature, in a preferred embodiment, a temperature sensor such as a thermistor 7 is encased in BONDiT BT45TG resin and placed in proximity to the anode and cathode. By proximity, what is meant is that it is close enough to provide an approximate measure of the temperature in the region of the electrodes. Appropriate temperature sensors, including those the employ a thermistor circuit that produces an output voltage related to temperature using software, are well known in the art. See, for example, the following U.S. Pat. No. 6,653,842 to Mosley, et al., U.S. Pat. No. 2,350,378 to Wallace, U.S. Pat. Nos. 3,959,087, 3,413,199 and 4,129,479 to Morrow, U.S. Pat. No. 2,382,734 to Marks, U.S. Pat. No. 3,902,982 to Nakagawa, U.S. Pat. No. 3,402,116 to Kaltenhauser, U.S. Pat. No. 4,940,946 to Nazaryan, and U.S. Pat. No. 4,224,154 to Steininger.

Figure 5:
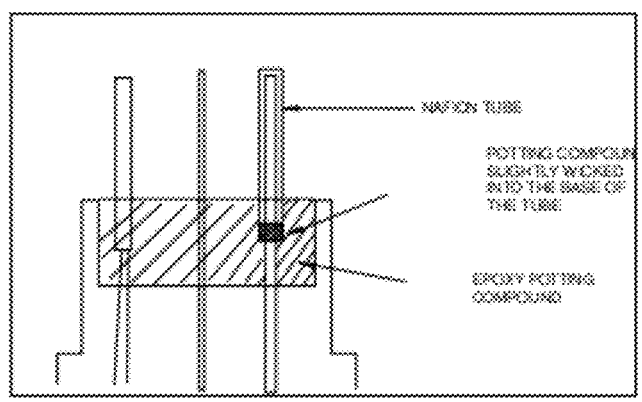
FIG. 5 is a cross-sectional view of the halogen sensor.

Nafion tubing, however, expands when it is exposed to water. Therefore, the sealing of the open end(s) of the Nafion tubing should accommodate this expansion without allowing water to leak through the seal as opposed to passing through the wall of the tubing. In the embodiment in which one end of the tube is exposed rather than seated in the base material with the other end (such as in the U- or V-shape configurations), this may be accomplished by sealing the exposed, open end of the Nafion tubing with the BONDiT resin noted above or a polyol resin such as manufactured by Alumite Corporation under the name Amazing Casting Resin and sealing the lower end in a base 5 with a flexible adhesive epoxy, such as manufactured by 3M and designated DP-270. See FIG. 4. In an embodiment, the epoxy is the material of the base 5 itself. The base 5, and thus the sensor, may be mounted in an electrically insulative housing 6 of a material that is chemically durable, such as PVC or other similar material that may be made of PVC, as illustrated in FIGS. 4 through 6. While the inventor does not wish to be bound to any particular theory, it is believed that the Polyol resin binds so well to the Nafion because hydroxyl groups of the polyols might fuse with the Nafion. The flexible adhesive epoxy is used for the lower end of the tubing because polyol resin does not seem to adhere properly to PVC housing in which the components are set.

In the embodiment in which only one end of the Nafion tube is affixed into the base 5, the Nafion tube is mounted in such a way that the lower end is properly sealed into the base 5 such as to maintain the seal during use and dimensional changes in the tube caused by exposure to water. If the tube is placed over the anode and sealed with the polyol resin before the base is potted air is trapped inside the tube and when the base is potted the epoxy will not wick up into the bottom of the tube allowing an air gap between the parts of the anode outside underneath the tube. If insufficiently flexible or Teflon-adhesive epoxies are used in place of the BONDiT resin to fill out the base of the tube once the tube is exposed to water, the adhesion is such that it collapses away from the epoxy around the outside and water transgresses around the bottom of the tube, bypassing the Nafion barrier. This leakage, then, mitigates the effect of the Nafion and the electrode does not achieve the full benefits ascribed to the Nafion covered anode as outlined. Therefore the area around the bottom of the electrodes is potted first and then the Nafion tube is placed over the anode and pushed into the epoxy before the polyol resin is applied, letting the epoxy wick up through the bottom of the tube. Once the epoxy is hardened the polyol resin is then applied over the tip of the anode and tube. See FIG. 4.

In the U- or V-shape configurations, as shown in FIG. 5, both ends of the tubing may be planted in the base 5 as described above with respect to the single end of the first embodiment. The Nafion tube is thus mounted in such a way that both ends are properly sealed in the base 5. Again, if insufficiently flexible or Teflon-adhesive epoxies are used in place of the BONDiT resin to fill out the base of the tube once the tube is exposed to water, the adhesion is such that it collapses away from the epoxy around the outside and water transgresses around the bottom of the tube, bypassing the Nafion barrier, mitigating the effect of the Nafion and the electrode.

Electrodes fabricated in such ways have been found to last at least several months with no degradation in signal.

By well-known, conventional signal conversion techniques, the measurement from the electrode is input into measurement and readout electronics that convert the signal into parts per million readings and compensate for temperature changes to which the electrode is also sensitive by means of a temperature sensor such as thermistor 7 incorporated into the sensor housing. The signal is then used to keep the sanitizer sensor output display relatively constant over a specified range of temperature by well-known methods. The measurement electronics also have conventional data logging and networking capabilities to provide enhanced functionality for control and monitoring systems.

Figure 8:
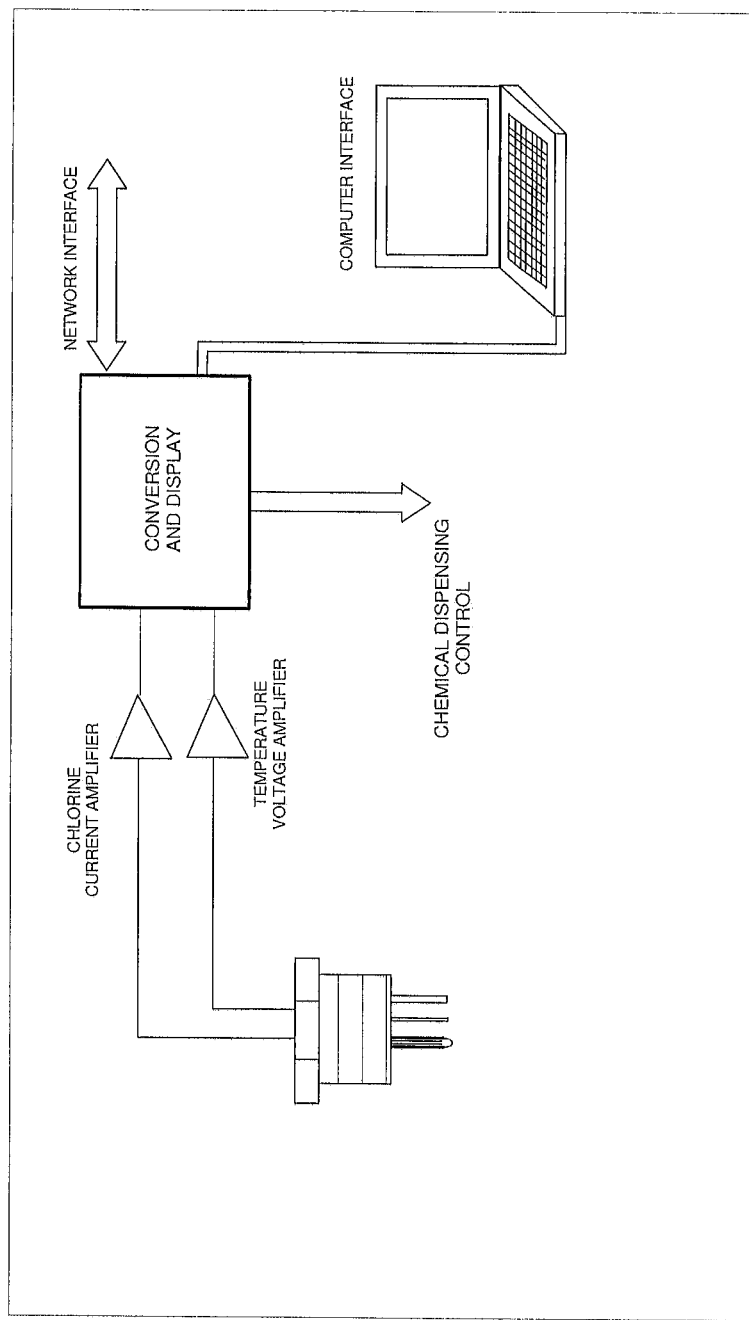
FIG. 8 is a schematic representation of the halogen sensor of this invention in combination with a readout device.

FIG. 8 illustrates a halogen sensor 11 in combination with a readout device. Electrical outputs from the sensor 11 are amplified by current from the halogen sensor being directed through a current amplifier 13 and output from the temperature sensor being directed through voltage amplifier 15. Outputs from the amplifiers are directed to a conversion and display unit 17 for translating the inputs into chlorine concentration and water temperature readings, the chlorine concentration reading being determined in view of the temperature. A computer interface 19 is employed to enter adjustments and desired settings into conversion and display unit 17, which also can control an automatic dispensing unit of halogen-adjustment chemical that supplies the pool or spa, etc., with the chemical.

pH Sensor

It also has been found that the pH measurement can be carried out by using the reference electrode discussed above as an anode and using, as a cathode, a rod of high purity antimony (say 99.999%)/antimony oxide or high purity bismuth/bismuth oxide (for simplicity, hereinafter reference will be made only to antimony) as described in U.S. Pat. No. 6,653,842 to Mosley, et al., incorporated herein by reference, but encased in a membrane 52 of a cation exchange fluoropolymer that is also impervious to oxygen and anions such as chlorine, such as Nafion tubing, in a manner as described above with respect to the anode. However, because the cathode used for pH measurement is preferably larger than the anode, the preferred Nafion tubing is larger than that for the anode. Thus, for example, the Nafion tubing for the antimony pH-measuring rods may be formed from Nafion sheets, such as Model Number TT-700, being the same Nafion 1100 equivalent weight material of the smaller tubes manufactured by Perma Pure.

Figure 9:
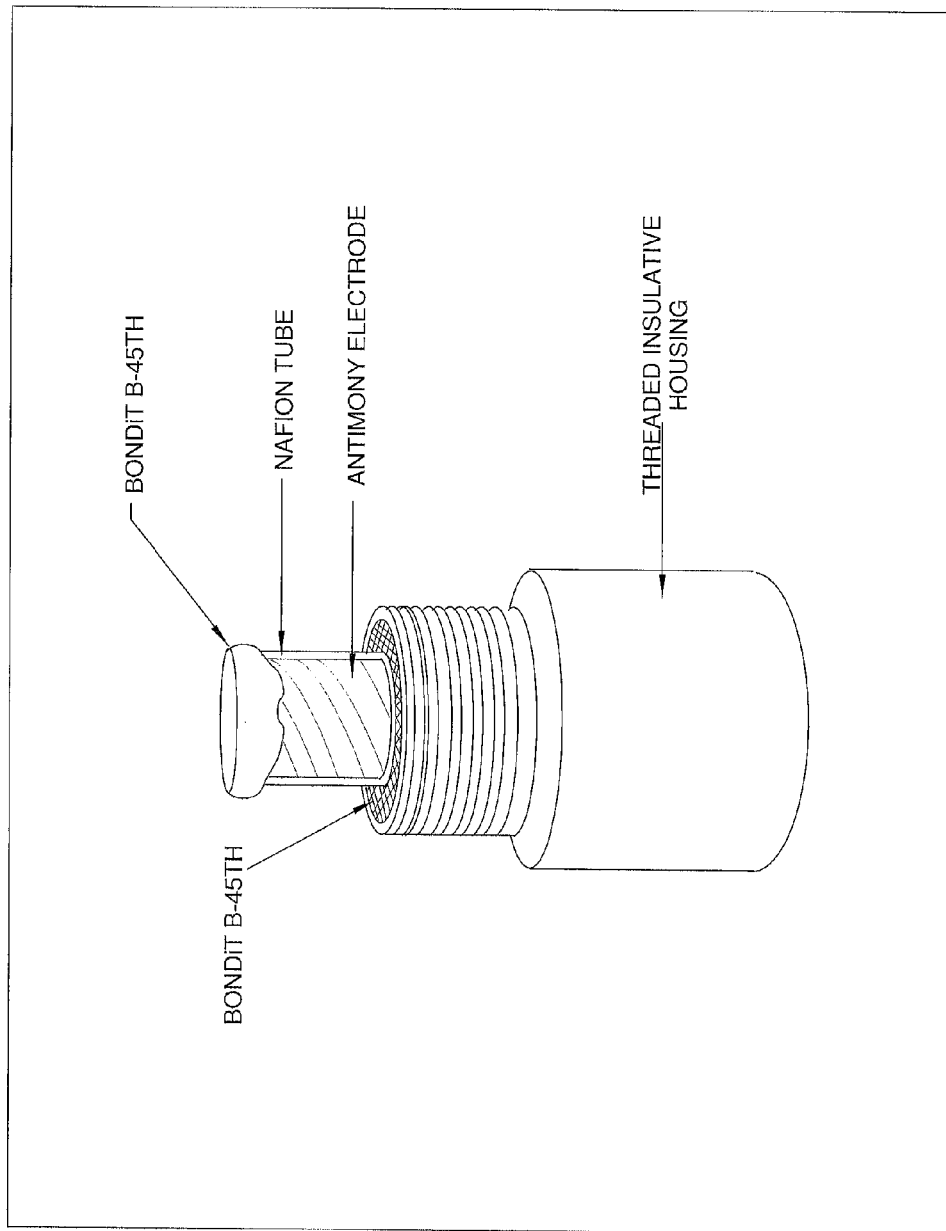
FIG. 9 is perspective view of a pH sensor of the present invention.

FIG. 9 illustrates a pH sensor of this invention, including the cathode 50 and the Nafion tubing 52. The pH sensor may be used in conjunction with a high stability and extremely low leakage gel-filled reference electrode of this invention, as described above. The pH sensing electrode comprises a large diameter antimony or other pH-sensitive material encased in a Nafion tube and, preferably used in combination with a substantially leak free reference electrode as described above.

As shown in FIG. 9, the sensor may be mounted in an electrically insulative housing 54 of a material that is chemically durable such as PVC or other similar material. Although any size and shape cathode may be formed from the antimony, antimony is crystalline and very brittle, and so electrodes formed into small rods of conventional dimensions can be quite fragile and exhibit larger electrical impedance due to the small surface area. This is overcome in the present invention by casting the antimony into a large-diameter, short, cylindrical rod approximately ⅝ inches in diameter and ½ inches in length. This results in a very rigid structure and increases the surface area of the antimony, providing much lower electrical impedance. It has been found that under normal circumstances, the minimum diameter for fairly good mechanical strength is about ⅜ inches and a maximum length of about ¾ inches, maintenance of the surface area being of particular interest.

Because of difficulties involved in manufacture, Nafion tubing is extruded in small inside diameters the largest of which is about 0.086 inches. Larger tubing is made by using a flat sheet of Nafion and forming it into tube shapes by rolling the sheet and forming a longitudinal seam. In an embodiment of the present invention, the inner diameter of the resulting tubing is about ⅝ inches, which conveniently accommodates the larger antimony rod employed to address the brittle nature of antimony. The Nafion, as discussed previously, swells when exposed to water so it becomes larger than the diameter of the antimony rod. While this enlargement may be used to fit the tubing over the cathode, it can also result in a visible gap between the antimony and the inner wall of the tubing. Nevertheless, this gap has not been observed to detract from the pH response, even over long-term use. However, the hydration period is longer (about 24 hrs) compared with what has been experienced with dip coatings of Nafion. Since all commercial sensors, as a matter of course, require a 24-hr stabilization time, the longer hydration period has little if any practical impact on pool measurements.

The open end of the Nafion tube 52 may be sealed with a leak-proof cap 56 of or with polyol resin or other appropriate sealant in the manner and with the considerations discussed above in connection with the open-end embodiment of the Nafion tube for the halide sensor.

The response mechanism of antimony to pH changes depends to some extent on the presence of oxygen. Thus, a small amount of oxygen is required for the antimony to respond to pH changes. According to the SJOBERG and G. NILSSON paper Dual mode antimony electrode for simultaneous measurements of PO2 and pH, *Acta Anaesthesiol Scand* 2000; 44: 32-36), that minimum amount of oxygen required for the acceptable pH response is slightly below 5%.

As discussed above, while Nafion is almost impermeable to oxygen, in practice oxygen is inevitably trapped inside the tubing when the electrode is made and an extremely small fraction does pass through the Nafion. The resulting measured response to pH changes for such Nafion tube-encased electrodes prepared as described herein has shown that the amount of oxygen inside the tube is sufficient for accurate pH measurement.

As also discussed above, however, oxygen can have a detrimental effect on pH measurement over time as well. This can lead to oxidation of the surface of the electrode, leading to diminishing pH sensitivity over time. Surprisingly, it has been found that the amount of oxygen inherently present in and/or passing through the tubing when the sensor is prepared according to the methods described herein is believed to be just enough to drive the pH response, yet not enough to oxidize the surface of the antimony—or at least not enough to oxide the surface of the antimony to an extent such as to interfere significantly with the pH measurements for at least several months.

The pH sensitivity is approximately −48 mV/pH, which is lower than the theoretical value according to the Nernst equation of −56.92 mV/pH, but sufficient to measure pH in swimming pools. By contrast, the pH sensitivity of dip-coated Nafion electrodes was found to be somewhat greater than that predicted by the Nernst equation, presumably owing to the much thinner coating of Nafion compared to the tube, and the results between batches of the dip-coated Nafion electrodes were highly variable. Thus, the Nafion-tube-enclosed electrodes tested all have had a much more consistent response between sensors in both sensitivity and offset, reducing the amount of tuning required in the electronics to cover the same span in pH measurement due to sensor changes.

The antimony electrode may be calibrated with either buffers or sample water at two different pH levels. Buffers suitable for antimony electrode calibration are tris (hydroxymethyl) aminomethane, and water containing mixtures of sodium bisulfate or muriatic acid and sodium bicarbonate. Buffers containing phosphates and other chemicals used in standard pH buffers used with glass electrodes are generally unsuitable for calibrating the Nafion tube-encased antimony electrode. In fact, calibrations using such buffers with both an antimony electrode and a glass electrode will result in different measurements at the same pH when immersed in pool water or other regular water samples.

The pH measurement with the antimony electrode is also temperature dependent. The temperature is sensed by a thermistor mounted in a thermally conductive tube next to or at least near enough to the antimony electrode to provide an indication of the temperature at the electrode and the signal from the thermistor is then used to keep the pH sensor output display relatively constant over a specified range of temperature. If the halide and pH sensors are mounted together in the same system or very close to each other only one temperature sensor is required as opposed to incorporating one into each sensor. Thus, in such case, thermistor 7 of the halide sensor can be used for both sensors.

While the present invention contemplates incorporation of the Nafion tubing with the electrode described in the U.S. patent to Mosley et al. noted above, and with the additional option of enlarging the electrode, that patent is instructive as to other remaining aspects and methods involving the Nafion tube-encased antimony or bismuth electrode of the present invention. Other U.S. patents of background assistance may be U.S. Pat. No. 4,818,365 to Kinlen, U.S. Pat. No. 3,298,944 to Luck, U.S. Pat. No. 3,258,682 to Maurer, U.S. Pat. No. 4,681,116 to Settler, U.S. Pat. No. 3,742,594 to Kleinberg, and U.S. Pat. No. 4,119,498 to Edwall.

Total Dissolved Solids (TDS) Sensor

Guidelines exist for the maximum amount of dissolved solids in drinking water and in pool or spa environments. In a pool environment, a high level of dissolved solids can interfere with the effectiveness of sanitizers, thereby allowing algae formation even when the sanitizers are at the recommended level. Some pools may use dissolved salts in the water to generate chlorine on site. These generators require a minimum amount of salt in the water to allow the chlorine generator to function properly. There are also certain conditions in a pool environment that may be difficult to diagnose without knowing the total amount of dissolved solids in the water of the pool.

Figure 10:
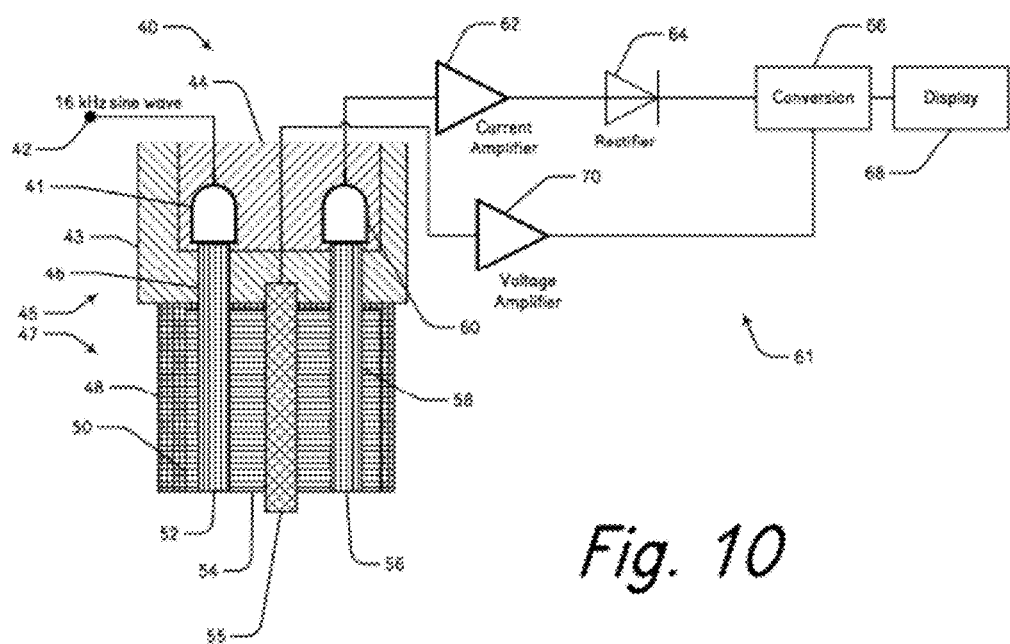
FIG. 10 is a cross-sectional view of a TDS sensor of this invention.

Thus, in some embodiments and referring to FIG. 10, a total dissolved solids (TDS) sensor 60 is provided to measure the amount of dissolved salt in a pool or spa environment. TDS sensor 60 includes an upper portion 65 and a lower portion 67. A pair of probe contacts 61 and 80 is provided within a compartment 64 within a protective outer shell 63 of upper portion 65 of TDS sensor 60. To avoid dependence upon special test strips or costly meters and probes, two titanium or stainless steel electrodes 66 and 78 are electrically connected to probe contacts 41 and 60, respectively. Electrodes 66 and 78 extend through outer shell 63 and through outer shell 68 of lower portion 67 of TDS sensor 60. Electrodes 66 and 78 are spaced apart in waterproof lower portion 67, which contains a potting compound 70 between and around electrodes 68 and 78 for waterproofing and electrical insulation. An end 72, 76 of each electrode 66, 78, respectively, is flush with end 74 of waterproof lower portion 78. (Titanium electrodes have the advantage of becoming passivated during use, thereby become more corrosion-resistant than stainless steel.)

A voltage is provided at 62 across spaced-apart electrodes 66, 78, for example, by a generator. In some embodiments, the voltage is a sine wave of about 16 kHz and is used to minimize polarization of spaced-apart electrodes 66, 78 that may occur were a DC voltage or a square wave of anything other than a 50% duty cycle to be used. The frequency of 16 kHz may vary in other embodiments, and can be selected by experimentally (or otherwise) obtaining a Bode plot of current amplifier 82, determining a frequency region having a flat frequency response, and selecting a frequency within the determined frequency region. The relatively high frequency provides a much higher gain bandwidth than is found in known TDS sensors and provides a greater response linearity over a wide range of TDS values found in pools with and without salt chlorination systems than is provided by known TDS sensors.

Measuring circuit 81 measures voltage between electrodes 66, 78. This voltage is a function of the amount of dissolved salt in the water into which probe portion 67 is immersed. The voltage is rectified by a rectifier 84 and fed to a converter 86 and thence to display 88. Some embodiments of the present invention provide two range options, HIGH and LOW, to accommodate the TDS measurements in pools and spas (e.g., LOW provides 0 to 3,000 ppm) and salt-chlorinated pools (e.g., HIGH provides 2,500 ppm to 6,000 ppm). Conversion circuit 86 converts the TDS measurement for display and/or processing purposes. In embodiments in which the measurement is temperature sensitive, the measurement is compensated as described in accordance with FIGS. 4-6 using temperature probe 75 and voltage amplifier 90.

Combination Measuring System

Figure 11:
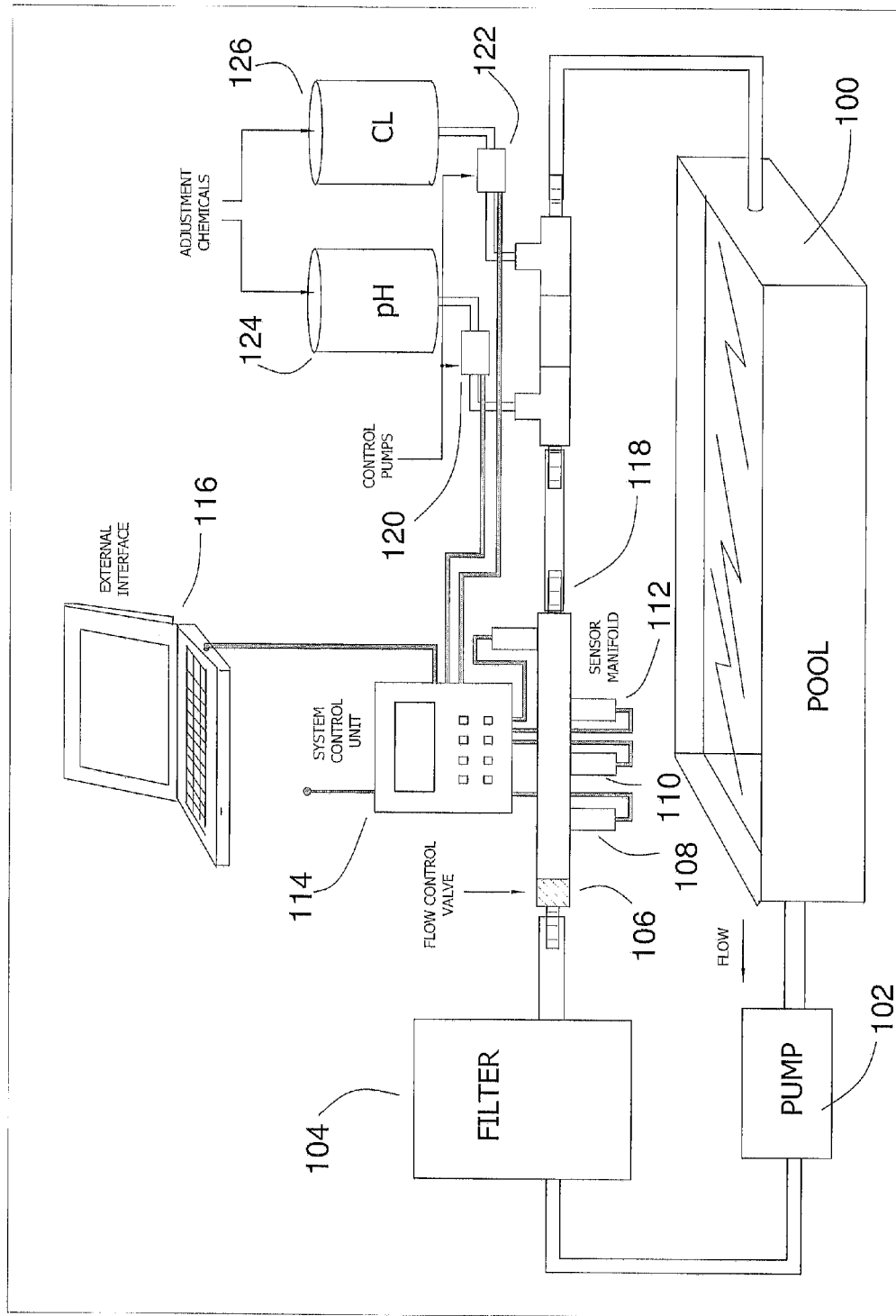
FIG. 11 is a schematic representation of a measurement and adjustment system of this invention.

As noted above, the various aspects of the present invention may be employed in combinations in any desired permutation. For example, the pH sensor may be used alone or in combination with the halogen sensor or the TDS sensor or both. Similarly, the halogen sensor may be used alone or in combination with the TDS sensor. The temperature sensor may be employed in any of such combinations. FIG. 11 illustrates, schematically, a complete measurement system combining all of the sensors and electrodes of the present invention in a pool treatment situation. As can be seen from FIG. 11, water from a pool 100 is pumped via pump 102 through a filter 104 and then a flow control valve 106, to the sensors 108, 110 and 112 of the present invention. The output from the sensors 108, 110 and 112 are sent to system control unit 114, also controlled by an external interface 116, which can enter adjustments and desired settings, such as desired pH or chlorine content of the pool water, into system control unit 114. The system control unit 114 controls sensor manifold 118 and control pumps 120 and 122, which, according to instructions from system control unit 114 (and external interface 116), meter pH-adjusting chemicals and chlorine from supply tanks 124 and 126, respectively, into the water pumped from the pool, after which the water is recycled back into pool 100.

The following examples illustrate various aspects of the present invention and are not intended to limit the scope of the present invention. Those of skill in the art should, in light of the present disclosure, appreciate that many changes can be made in the specific embodiments which are disclosed and still obtain a like or similar result without departing from the spirit and scope of the invention.

EXAMPLE 1

The effect of pool water on a pair of bare platinum electrodes was evaluated in field tests at several pool sites with the sensors interfaced to a continuous monitoring system. When the signals became degraded, in three weeks, the electrodes were removed and the electrodes were scanned with an electron microscope and EDA scans were taken of elements on the anodes. It was clearly visible that the bare platinum anode had accumulated contaminants on the surface and that the major constituent of the elements on the surface was oxygen. The oxygen peak was roughly twice as high as the platinum peak. These findings were in stark contrast to the findings for the platinum cathode. The cathodes were found to be free of almost all contaminants and the surfaces were found to be almost pure platinum with no oxygen.

EXAMPLE 2

A method to protect the anode was used similar to that described in U.S. Pat. No. 4,818,365 to Kinlen. Several dip coatings of Nafion copolymer 5% wt in lower aliphatic alcohols and water were applied to the electrodes. Nafion was chosen in that it is impermeable to oxygen and has low electrical resistance. The electrodes were placed back in the field for several weeks and reexamined. The platinum under the coating was found to be free of contaminants comparable to the cathode. A Nafion scan showed some iron and carbon, the carbon most likely being from the Nafion. The Nafion itself, however, was clearly damaged from the exposure. Although the electrode signal stayed relatively high during the trial it was obvious that the Nafion coating was not durable enough to withstand continuous use in pools. The main difficulty with the Nafion dip coating on platinum appeared to be the lack of adhesion of it to the metal surface.

EXAMPLE 3

Experiments were conducted using arrangements of electrodes of titanium and platinum coated with Nafion tubing as taught in Mosier et al. patent application Ser. No. 10/848,196. Such electrodes displayed no marked sensitivity to chlorine/bromine. The titanium passivated quickly with respect to cathodic and anodic currents generated by the reduction of oxidizing chemicals. The result of the impermeability of Nafion to chlorine and bromine was that there was no response to the presence or chlorine or bromine when both electrodes were covered with the Nafion. Therefore, it is clear that such an arrangement of electrodes as discussed by Mosier et al. is not suitable to measure chlorine or bromine in pools or spas.

EXAMPLE 4

Figure 7:
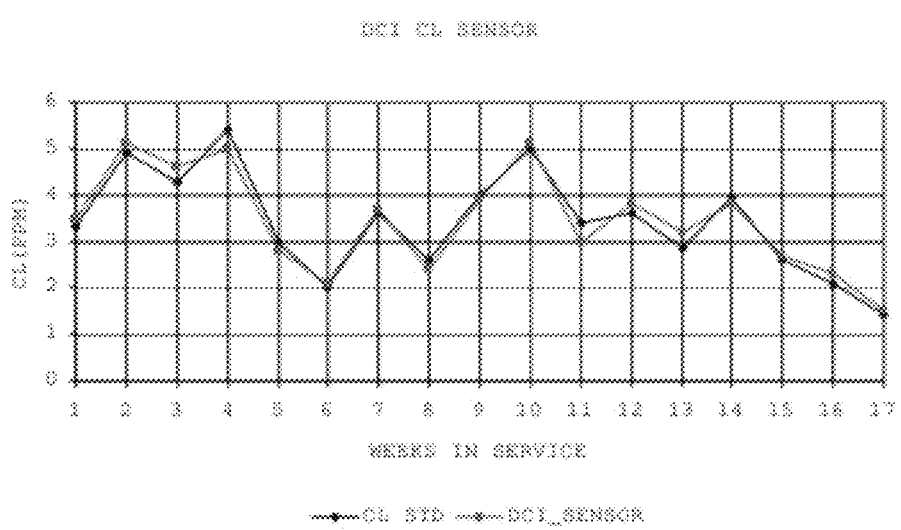
FIG. 7 is a graph of the response (in terms of chlorine concentration versus time) of the chlorine sensor according to the present invention over a period of months in a spa in comparison to that of a Severn Trent MicroChem2 with a series 4000 measuring cell.
Figure 12:
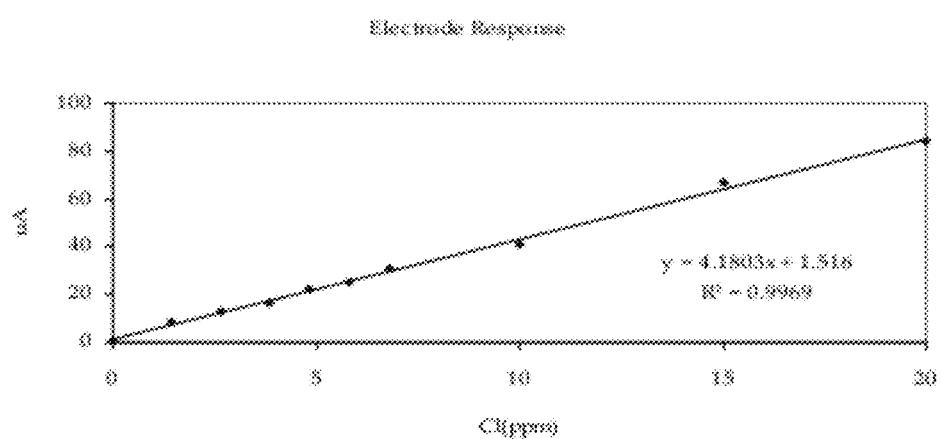
FIG. 12 is a graph of the chlorine response of a chlorine sensor of the present invention in terms of microAmps versus the chlorine concentration.

FIG. 12 is a graph of the chlorine response of a chlorine sensor of the present invention in terms of microAmps versus the chlorine concentration, showing a nearly linear correlation over the concentrations of interest. FIG. 7 shows a graph of the response of the chlorine sensor according to the present invention over a period of months in a spa. The signal was tracked against a Severn Trent MicroChem2 with a series 4000 measuring cell. The 4000 measuring cell contains corundum as an abrasive cleaning mechanism around the electrodes. As the graph illustrates, the sensor of the present invention exhibited no loss of output with respect to the commercial system. Since the measurement requires a constant flowrate there is provided a constant flow regulator as depicted in FIG. 11. The flowrate is regulated by means of a small insert into the end of the sensor manifold and is similar to flow regulators used in kitchen faucets where the flow is limited to ~1 GPM. A bias voltage of 1V which is in the range of reduction potentials of chlorine is applied between the electrodes. A somewhat lower voltage can be used for bromine since its reduction potential is ~350 mV. It is our finding that in a swimming environment, contrary to the findings of Marks and Bannister that the relationship between oxidizer concentration and the resultant current flow has been found to be linear up to at least 20 ppm. This is well above the generally accepted levels of residual chlorine/bromine in commercial and residential pools and spas.

All references, including without limitation all papers, publications, presentations, texts, reports, manuscripts, brochures, internet postings, journal articles, periodicals, and the like, cited in this specification are hereby incorporated by reference. The discussion of the references herein is intended merely to summarize the assertions made by their authors and no admission is made that any reference constitutes prior art. The inventors reserve the right to challenge the accuracy and pertinence of the cited references.

It is intended that all patentable subject matter disclosed herein be claimed and that no such patentable subject matter be dedicated to the public. Thus, it is intended that the claims be read broadly in light of that intent. In addition, unless it is otherwise clear to the contrary from the context, it is intended that all references to "a" and "an" and subsequent corresponding references to "the" referring back to the antecedent basis denoted by "a" or "an" are to be read broadly in the sense of "at least one." Similarly, unless it is otherwise clear to the contrary from the context, the word "or," when used with respect to alternative named elements is intended to be read broadly to mean, in the alternative, any one of the named elements, any subset of the named elements or all of the named elements.

In view of the above, it will be seen that the several advantages of the invention are achieved and other advantageous results obtained. It should be understood that the aforementioned embodiments are for exemplary purposes only and are merely illustrative of the many possible specific embodiments that can represent applications of the principles of the invention. Thus, as various changes could be made in the above methods and compositions without departing from the scope of the invention, it is intended that all matter contained in the above description as shown in the accompanying drawings shall be interpreted as illustrative and not in a limiting sense.

Moreover, one of ordinary skill in the art can make various changes and modifications to the invention to adapt it to various usages and conditions, including those not specifically laid out herein, without departing from the spirit and scope of this invention. Accordingly, those changes and modifications are properly, equitably, and intended to be, within the full range of equivalents of the invention disclosed and described herein.

What is claimed is:

1. A chlorine sensor comprising a gold cathode and a platinum anode, the platinum anode being sealed inside a low electrical resistance, water-permeable membrane comprising a tube having a wall thickness of at least 0.004 inches, wherein the tube provides a barrier for the platinum anode to both oxygen and anions, and wherein the tube comprises a copolymer of tetrafluoroethylene.

2. The chlorine sensor of claim 1 wherein the tube comprises a copolymer of tetrafluoroethylene and perfluoro-3,6-dioxa-4-methyl-7-octene-sulfonic acid.

3. A halogen sensor comprising a metal anode, the metal anode being sealed inside a low electrical resistance, water-permeable membrane comprising a tube having a wall thickness of at least 0.004 inches, wherein the tube provides a barrier for the metal anode to both oxygen and anions, and wherein the tube comprises a copolymer of tetrafluoroethylene, and a metal cathode.

4. The halogen sensor of claim 1 wherein the metal anode is platinum.

5. The halogen sensor of claim 1 wherein the metal cathode is gold.

6. The halogen sensor of claim 1 wherein the halogen is chlorine.

7. The halogen sensor of claim 6 further comprising a bias voltage source configured for applying a voltage between the anode and the cathode.

8. The halogen sensor of claim 7 wherein a positive voltage is applied to the anode and a negative voltage is applied to the cathode.

9. The halogen sensor of claim 8 wherein the positive voltage is 1 volt.

10. The halogen sensor of claim 3 wherein the halogen is bromine.

11. The halogen sensor of claim 10 comprising a voltage source configured for applying a bias voltage of 350 millivolts between the anode and the cathode, wherein a positive voltage is applied to the anode and a negative voltage is applied to the cathode.

12. The halogen sensor of claim 3 wherein the tube is configured to prevent exposure of the anode to ambient oxygen exterior to the tube, except as may pass through the tube.

13. The halogen sensor of claim 3 wherein the tube is configured to minimize exposure of the anode to ambient oxygen exterior to the tube.

14. The halogen sensor of claim 3 wherein the tube has sealed ends and has a wall thickness not greater than 0.006 inches.

15. The halogen sensor of claim 14 further comprising a base material in which at least one end of the tube is sealed in the base material, and an electrically insulative housing supporting the base material.

16. The halogen sensor of claim 14 further comprising a base material and wherein the cathode, the anode, and the tube are configured in a U-shape or V-shape, such that both ends of the anode, the cathode and the tube are within the base material.

17. The halogen sensor of claim 3 further comprising a temperature sensitive element in proximity to the cathode and anode such that the temperature sensitive element provides an indication of temperature corresponding to a temperature of the anode and the cathode.

18. The halogen sensor of claim 17 wherein the temperature sensitive element is a thermistor in a resin sealant.

19. The halogen sensor of claim 17 further comprising a device connected to the anode and the cathode for monitoring a chlorine concentration in an aquatic environment and for controlling a chlorine concentration in the aquatic environment.

20. The halogen sensor of claim 19 wherein the device comprises a current amplifier and a voltage amplifier wherein an electrical output from the halogen sensor is provided to the current amplifier and an electrical output from the temperature sensitive element is provided to the voltage amplifier.

21. The halogen sensor of claim 20 further comprising a conversion unit for translating outputs from the amplifiers into chlorine concentration indication and a water temperature indication and a display unit for displaying the indications wherein the chlorine concentration indication is determined as a function of the water temperature indication.

22. The halogen sensor of claim 21 further comprising a dispensing unit responsive to the device for dispensing a halogen-adjustment chemical that supplies the aquatic environment with the halogen-adjustment chemical.

23. The halogen sensor of claim 22 further comprising a computer interface for inputting into the conversion unit at least one of (1) adjustments for controlling the dispensing unit and (2) a desired setting for controlling the dispensing unit.

24. The halogen sensor of claim 3 wherein the tube comprises a copolymer of tetrafluoroethylene and perfluoro-3,6-dioxa-4-methyl-7-octene-sulfonic acid.

25. A method of making a halogen sensor comprising the steps of:
providing a metal anode,
providing a low electrical resistance, water-permeable tube comprising a copolymer of tetrafluoroethylene having a low electrical resistance, having water-permeability, and having a wall thickness of at least 0.004 inches, and
sealing the metal anode inside the tube so that the tube provides a barrier for the metal anode to both oxygen and anions.

26. The method of claim 25 wherein the metal anode is platinum.

27. The method of claim 25 wherein the metal cathode is gold.

28. The method of claim 25 wherein the halogen is chlorine.

29. The method of claim 20 further comprising the step of providing a bias voltage source configured for applying a voltage between the anode and the cathode.

30. The method of claim 29 wherein the bias voltage source is configured to apply a positive voltage to the anode and a negative voltage is applied to the cathode.

31. The halogen sensor of claim 25 further comprising the step of sealing each end of the tube.

32. The method of claim 31 further comprising providing a base material, sealing at least one end of the tube in the base material, and providing an electrically insulative housing supporting the base material.

33. The method of claim 31 further comprising providing a base material and wherein the cathode, the anode, and the tube are configured in a U-shape or V-shape, positioning both ends of the anode, the cathode and the tube within the base material.

34. The method of claim 25 further comprising providing a temperature sensitive element in proximity to the cathode and anode wherein the temperature sensitive element is configured to provide an indication of temperature corresponding to a temperature of the anode and the cathode.

* * * * *

UNITED STATES PATENT AND TRADEMARK OFFICE
CERTIFICATE OF CORRECTION

Page 1 of 1

PATENT NO.        : 8,574,413 B2
APPLICATION NO.   : 13/051106
DATED             : November 5, 2013
INVENTOR(S)       : Michael D. Mosley and Paul Decker It is certified that error appears in the above-identified patent and that said Letters Patent is hereby corrected as shown below:

In the Claims

Column 27, Claim 4, Line 64: "1" should read -- 3 --.

Column 27, Claim 5, Line 66: "1" should read -- 3 --.

Column 28, Claim 6, Line 1: "1" should read -- 3 --.

Signed and Sealed this
Seventeenth Day of February, 2015

Michelle K. Lee
*Deputy Director of the United States Patent and Trademark Office*